(12) United States Patent
Chivukula et al.

(10) Patent No.: US 10,836,753 B2
(45) Date of Patent: Nov. 17, 2020

(54) CO-CRYSTALS OF SGLT2 INHIBITORS, PROCESS FOR THEIR PREPARATION AND PHARMACEUTICAL COMPOSITIONS THEREOF

(71) Applicant: Laurus Labs Ltd., Hyderabad (IN)

(72) Inventors: Kameswar Rao Chivukula, Hyderabad (IN); Ram Thaimattam, Hyderabad (IN); Veeranarayana Bandlamudi, Hyderabad (IN); Durga Visweswar Rao Padala, Hyderabad (IN); Narapa Reddy Gade, Hyderabad (IN); Nageswar Rao Regandla, Hyderabad (IN); Sivarami Reddy Yasam, Hyderabad (IN); Venkata Rama Krishna Murthy Moturu, Hyderabad (IN); Venkata Sunil Kumar Indukuri, Hyderabad (IN); Uma Maheswar Rao Vasireddi, Hyderabad (IN); Srihari Raju Kalidindi, Hyderabad (IN); Satyanarayana Chava, Hyderabad (IN)

(73) Assignee: Laurus Labs Limited, Hyderabad (IN)

( * ) Notice: Subject to any disclaimer, the term of this patent is extended or adjusted under 35 U.S.C. 154(b) by 0 days.

(21) Appl. No.: 16/530,521

(22) Filed: Aug. 2, 2019

(65) Prior Publication Data

US 2019/0352290 A1 Nov. 21, 2019

Related U.S. Application Data

(62) Division of application No. 15/759,562, filed as application No. PCT/IB2016/055495 on Sep. 15, 2016, now Pat. No. 10,428,053.

(30) Foreign Application Priority Data

| Sep. 15, 2015 | (IN) | ............................ 4903/CHE/2015 |
| Mar. 28, 2016 | (IN) | .............................. 201641010442 |
| Aug. 29, 2016 | (IN) | .............................. 201641029280 |

(51) Int. Cl.
| C07D 409/10 | (2006.01) |
| C07D 241/24 | (2006.01) |
| C07D 213/80 | (2006.01) |
| A61P 3/10 | (2006.01) |
| A61K 31/7048 | (2006.01) |
| C07D 407/12 | (2006.01) |
| C07D 309/10 | (2006.01) |
| C07D 211/60 | (2006.01) |

(52) U.S. Cl.
CPC ........ *C07D 409/10* (2013.01); *A61K 31/7048* (2013.01); *A61P 3/10* (2018.01); *C07D 211/60* (2013.01); *C07D 213/80* (2013.01); *C07D 241/24* (2013.01); *C07D 309/10* (2013.01); *C07D 407/12* (2013.01)

(58) Field of Classification Search
CPC .......................... C07D 409/10; A61K 31/7048
See application file for complete search history.

(56) References Cited

U.S. PATENT DOCUMENTS

| 6,515,117 | B2 | 2/2003 | Ellsworth et al. |
| 6,774,112 | B2 | 8/2004 | Gougoutas |
| 7,375,213 | B2 | 5/2008 | Deshpande et al. |
| 7,579,449 | B2 | 8/2009 | Eckhardt et al. |
| 7,723,309 | B2 | 5/2010 | Himmelsbach et al. |
| 7,919,598 | B2 | 4/2011 | Gougoutas et al. |
| 7,932,379 | B2 | 4/2011 | Deshpande et al. |
| 7,943,582 | B2 | 5/2011 | Nomura et al. |
| 7,943,788 | B2 | 5/2011 | Nomura et al. |
| 8,999,941 | B2 | 4/2015 | Henschke et al. |
| 9,006,188 | B2 | 4/2015 | Marom et al. |
| 9,024,009 | B2 | 5/2015 | Abdel-Magid et al. |
| 9,035,044 | B2 | 5/2015 | Nguyen et al. |
| 9,676,741 | B1 | 6/2017 | Santra et al. |
| 10,428,053 | B2 * | 10/2019 | Chivukula ........... C07D 309/10 |
| 2015/0307540 | A1 | 10/2015 | Dwivedi et al. |

FOREIGN PATENT DOCUMENTS

| CN | 102167715 A | 8/2011 |
| CN | 103965267 A | 8/2014 |
| IN | 1985/MUM/2013 | 5/2015 |
| WO | WO-02/083066 A2 | 10/2002 |
| WO | WO-2004/063209 A2 | 7/2004 |
| WO | WO-2008/002824 A1 | 1/2008 |
| WO | WO-2007/114475 A1 | 8/2009 |
| WO | WO-2012/163546 A1 | 12/2012 |
| WO | WO-2013/064909 A2 | 5/2013 |
| WO | WO-2013/079501 A1 | 6/2013 |
| WO | WO-2014/178040 A1 | 11/2014 |
| WO | WO-2015/040571 A1 | 3/2015 |
| WO | WO-2015/071761 A2 | 5/2015 |
| WO | WO-2015/104658 A2 | 7/2015 |
| WO | WO-2015/132803 A2 | 9/2015 |
| WO | WO-2015/198227 A1 | 12/2015 |
| WO | WO-2016/018024 A1 | 2/2016 |

* cited by examiner

*Primary Examiner* — Golam M Shameem
(74) *Attorney, Agent, or Firm* — Blank Rome LLP

(57) ABSTRACT

The present invention provides solid forms of SGLT2 inhibitors, to processes for their preparation and their use in the purification of SGLT2 inhibitors and also provided pharmaceutical compositions comprising them and their use in therapy.

3 Claims, 24 Drawing Sheets

CO-CRYSTALS OF SGLT2 INHIBITORS, PROCESS FOR THEIR PREPARATION AND PHARMACEUTICAL COMPOSITIONS THEREOF

CROSS-REFERENCE TO RELATED APPLICATIONS

This application is a divisional of and claims the benefit of the filing date of U.S. patent application Ser. No. 15/759,562, filed on Mar. 13, 2018, which is a national stage application of and claims the benefit of International Application PCT/IB2016/055495, filed on Sep. 15, 2016, which is based on and claims the benefit of Indian Provisional Application Nos. 4903/CHE/2015 filed on Sep. 15, 2015, entitled "Co-crystals of SGLT2 inhibitors, process for their preparation and pharmaceutical compositions thereof; IN201641010442 filed on Mar. 28, 2016, entitled "Solid forms of dapagliflozin, process for its preparation and pharmaceutical compositions thereof"; and IN201641029280 filed on Aug. 29, 2016, entitled "Solid forms of empagliflozin, process for its preparation and pharmaceutical compositions thereof"; the content of each of which are incorporated by reference herein.

FIELD OF THE INVENTION

The present invention relates to solid forms of SGLT1 inhibitors, processes for their preparation and use of such solid forms in pharmaceutical compositions and to their use in therapy. In particular, the present invention relates to solid forms of SGLT2 inhibitors, including their co-crystals, solvates and/or their polymorphs, process for their preparation and a pharmaceutical composition comprising the same.

BACKGROUND OF THE INVENTION

Diabetes mellitus is a serious and chronic metabolic disease that is characterized by high blood glucose (hyperglycemia) and affects millions of people worldwide. SGLT2 is a Sodium-dependent Glucose co-Transporter protein, which affects the reabsorption of glucose in the kidney. It is estimated that 90% of renal glucose reabsorption is facilitated by SGLT2. Since glucose reabsorption is mediated predominantly by SGLT2 and because high glucose levels have been identified as a cause of disease in diabetes, SGLT2 has become a drug target for type 2 diabetes therapy. Selective inhibition of SGLT2 has the potential to reduce hyperglycemia by inhibiting glucose reabsorption in the kidney with elimination of glucose by excretion in the urine (glucosuria).

Sodium-glucose co-transporter 2 (SGLT2) inhibitors are a new class of diabetic medications indicated only for the treatment of type 2 diabetes. In conjunction with exercise and a healthy diet, they can improve glycemic control. They have been studied alone and with other medications including metformin, sulfonylureas, pioglitazone, DPP-4 inhibitors and insulin.

Drugs in the SGLT2 inhibitors class include, but are not limited to canagliflozin, dapagliflozin, empagliflozin and the like. The structures of these SGLT2 inhibitors are represented below:

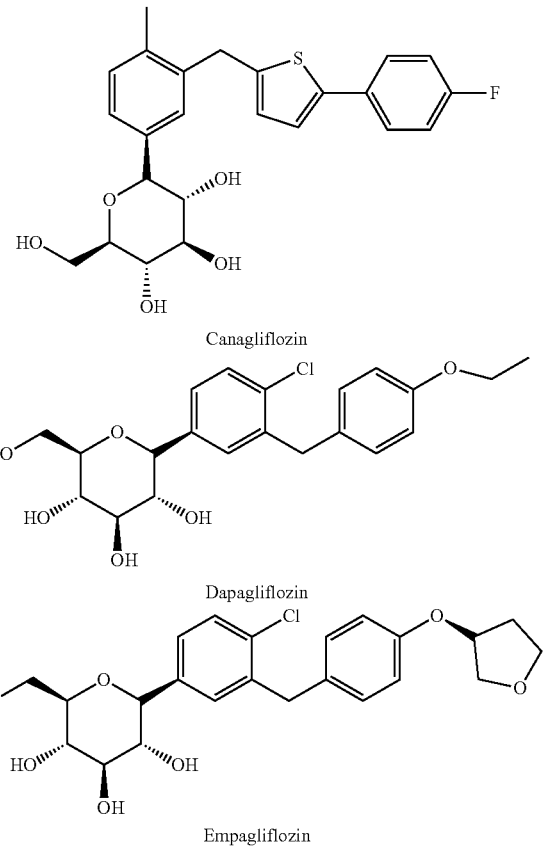

Canagliflozin

Dapagliflozin

Empagliflozin

SGLT2 inhibitor compounds and their preparation process have been described in the art, for example U.S. Pat. No. 7,943,788 disclosed canagliflozin; U.S. Pat. No. 6,515,117 disclosed dapagliflozin and U.S. Pat. No. 7,579,449 disclosed empagliflozin.

Solid forms of SGLT2 inhibitor compounds in the form of crystalline forms, solvates, co-crystals, eutectic mixtures etc. have been described in the art on various occasions, e.g. U.S. Pat. Nos. 6,774,112, 7,723,309, 7,919,598, 7,943,582, 9,006,188, 9,035,044, WO 2002083066, WO2004063209, WO2007114475, WO2008002824, WO2013064909, WO2012163546, WO2013079501, WO2014178040, WO2015071761, WO2015132803, WO2015198227, WO2016018024, US2015307540, IN1985/MUM/2013, CN102167715B and CN103965267A.

Further, amorphous form of dapagliflozin has been described in the art, for example in U.S. Pat. No. 8,999,941; PCT Publication Nos. WO 2015/104658, WO 2015/132803 and WO 2015/040571.

Obtaining suitable solid forms of a drug is a necessary stage for many orally available drugs. Suitable solid forms possess the desired properties of a particular drug. Such suitable forms often possess more favorable pharmaceutical and pharmacological properties or may be easier to process than known forms of the drug itself or may be used as a drug product intermediate during the preparation of the drug. For example, new drug formulations comprising crystalline forms of a given drug may have superior properties, such as solubility, dissolution, hygroscopicity and storage stability over existing formulations of the drug.

Discovering new polymorphic forms, solvates or co-crystals of a pharmaceutical product can provide materials having desirable processing properties, such as ease of handling, ease of processing, storage stability, and ease of purification or as desirable intermediate forms that facilitate conversion to other solid-state forms. New polymorphic forms, solvates or co-crystals of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., better processing or handling characteristics, better purity, improved dissolution profile, or improved shelf-life.

A co-crystal of a drug is a distinct chemical composition between the drug and the co-crystal former, and generally possesses distinct crystallographic and spectroscopic properties when compared to those of the drug and the co-crystal former individually. Unlike salts, which possess a neutral net charge, but which are comprised of charge-balanced components, co-crystals are comprised of neutral species. Thus, unlike a salt, one cannot determine the stoichiometry of a co-crystal former based on charge balance. Indeed, one can often obtain co-crystals having stoichiometric ratios of drug to the co-crystal former of greater than or less than 1:1. The stoichiometric ratio of an API to co-crystal former is a generally unpredictable feature of a co-crystal.

In view of the foregoing, it would be desirable to provide new solid forms of SGLT2 inhibitors. Further, it would be desirable to have reliable processes for producing these solid forms. Therefore, the present invention addresses the need in the art for pharmaceutically useful solid forms of SGLT2 inhibitor that may have improved physicochemical properties, such as a higher solubility and dissolution rate, enhanced flow properties and enhanced stability.

Although processes have been described in the art for the preparation of amorphous dapagliflozin, there still remains a need for simple, environmental-friendly, stable, economical and industrially feasible and scalable processes for the preparation of dapagliflozin amorphous form.

SUMMARY OF THE INVENTION

Accordingly, the present invention provides solid forms of SGLT2 inhibitors, including its co-crystals, solvates and/or polymorphs, processes for their preparation, pharmaceutical compositions containing the same and to their use in therapy.

In particular, the present invention relates to solid forms of SGLT2 inhibitors, wherein the SGLT2 inhibitor can be, but is not limited to canagliflozin, dapagliflozin, empagliflozin and the like, processes for their preparation and pharmaceutical compositions.

In accordance with another embodiment, the present invention provides solid forms of SGLT2 inhibitors, which are characterized by one or more of analytical techniques such as powder X-Ray diffraction (XRD); $^1$H NMR Spectrum; infrared spectrum (IR), differential scanning calorimetry (DSC) and/or thermogravimetric analysis (TGA), among others.

In accordance with one embodiment, the present invention provides novel co-crystals of SGLT2 inhibitors.

In accordance with another embodiment, the present invention provides the solid forms of SGLT2 inhibitors exist in the form of co-crystals, solvates, polymorphs of co-crystals or polymorphs of solvates.

In accordance with another embodiment, the present invention provides co-crystals of SGLT2 inhibitors, wherein the SGLT2 inhibitor is selected from canagliflozin, dapagliflozin, empagliflozin and the like.

In accordance with another embodiment, the present invention provides co-crystals of SGLT2 inhibitors and a co-crystal former, wherein the co-crystal former is selected from the group comprising DL-pipecolic acid, D-pipecolic acid, L-pipecolic acid, ammonia, nicotinic acid, isonicotinic acid, pyridine, pyrazole, pyrazine-2-carboxylic acid, imidazole, morpholine, proline and the like.

In accordance with another embodiment, the present invention provides co-crystals of SGLT2 inhibitors, wherein the SGLT2 inhibitor is selected from canagliflozin, dapagliflozin, empagliflozin and the like and co-crystal former is selected from the group comprising DL-pipecolic acid, D-pipecolic acid, L-pipecolic acid, ammonia, nicotinic acid, isonicotinic acid, pyridine, pyrazole, pyrazine-2-carboxylic acid, imidazole, morpholine, proline and the like.

In accordance with another embodiment, the present invention provides a process for the preparation of co-crystals of SGLT2 inhibitors, comprising:
  a) providing a solution or suspension comprising SGLT2 inhibitor and a co-crystal former in one or more solvents; and
  b) isolating the co-crystals of SGLT2 inhibitors; wherein the SGLT2 inhibitor is selected from canagliflozin, dapagliflozin and empagliflozin and wherein the co-crystal former is selected from the group comprising DL-pipecolic acid, D-pipecolic acid, L-pipecolic acid, ammonia, nicotinic acid, isonicotinic acid, pyridine, pyrazole, pyrazine-2-carboxylic acid, imidazole, morpholine, proline and the like.

In accordance with another embodiment, the present invention provides co-crystals of SGLT2 inhibitors, wherein the SGLT2 inhibitor is Canagliflozin.

In accordance with another embodiment, the present invention provides co-crystals of canagliflozin and a co-crystal former, wherein the co-crystal former is selected from the group comprising DL-pipecolic acid, D-pipecolic acid, L-pipecolic acid, ammonia, nicotinic acid, isonicotinic acid, pyridine, pyrazole, pyrazine-2-carboxylic acid, imidazole, morpholine and the like.

In accordance with another embodiment, the present invention provides co-crystal of canagliflozin and a co-crystal former, wherein the co-crystal former is selected from the group comprising DL-pipecolic acid, D-pipecolic acid, L-pipecolic acid, nicotinic acid, pyrazine 2-carboxylic acid, ammonia or pyrazole.

In accordance with another embodiment, the present invention provides canagliflozin DL-pipecolic acid co-crystal.

In accordance with another embodiment, the present invention provides canagliflozin DL-pipecolic acid co-crystal characterized by X-Ray powder diffraction (PXRD) pattern substantially in accordance with FIG. 01.

In accordance with another embodiment, the present invention provides canagliflozin DL-pipecolic acid co-crystal characterized by a $^1$H NMR Spectrum substantially in accordance with FIG. 02.

In accordance with another embodiment, the present invention provides canagliflozin DL-pipecolic acid co-crystal characterized by a differential scanning calorimetry (DSC) thermogram substantially in accordance with FIG. 03.

In accordance with another embodiment, the present invention provides canagliflozin DL-pipecolic acid co-crystal characterized by a thermogravimetric analysis (TGA) curve substantially in accordance with FIG. 04.

In accordance with another embodiment, the present invention provides Canagliflozin DL-pipecolic acid co-crystal characterized by an Infrared spectroscopy (IR) spectrum substantially in accordance with FIG. 05.

In accordance with another embodiment, the present invention provides Canagliflozin DL-pipecolic acid co-crystal characterized by one or more of the following: a powder X-Ray diffraction (XRD) pattern substantially in accordance with FIG. 01; a $^1$H NMR Spectrum substantially in accordance with FIG. 02; a differential scanning calorimetry (DSC) thermogram substantially in accordance with FIG. 03; a thermogravimetric analysis (TGA) curve substantially in accordance with FIG. 04 and/or an Infrared spectroscopy (IR) spectrum substantially in accordance with FIG. 05.

In accordance with another embodiment, the present invention provides a process for the preparation of Canagliflozin DL-pipecolic acid co-crystal, comprising providing a solution or suspension comprising canagliflozin and DL-pipecolic acid in one or more organic solvents and isolating the canagliflozin DL-pipecolic acid co-crystal.

In accordance with another embodiment, the present invention provides canagliflozin L-pipecolic acid co-crystal.

In accordance with another embodiment, the present invention provides a process for the preparation of Canagliflozin L-pipecolic acid co-crystal, comprising providing a solution or suspension comprising canagliflozin and L-pipecolic acid in one or more organic solvents and isolating the canagliflozin L-pipecolic acid co-crystal.

In accordance with another embodiment, the present invention provides canagliflozin D-pipecolic acid co-crystal.

In accordance with another embodiment, the present invention provides a process for the preparation of Canagliflozin D-pipecolic acid co-crystal, comprising providing a solution or suspension comprising canagliflozin and D-pipecolic acid in one or more organic solvents and isolating the canagliflozin D-pipecolic acid co-crystal.

In accordance with another embodiment, the present invention provides canagliflozin nicotinic acid co-crystal.

In accordance with another embodiment, the present invention provides a process for the preparation of Canagliflozin nicotinic acid co-crystal, comprising providing a solution or suspension comprising canagliflozin and nicotinic acid in one or more organic solvents and isolating the canagliflozin nicotinic acid co-crystal.

In accordance with another embodiment, the present invention provides canagliflozin pyrazine-2-carboxylic acid co-crystal.

In accordance with another embodiment, the present invention provides a process for the preparation of Canagliflozin pyrazine-2-carboxylic acid co-crystal, comprising providing a solution or suspension comprising canagliflozin and pyrazine-2-carboxylic acid in one or more organic solvents and isolating the canagliflozin pyrazine-2-carboxylic acid co-crystal.

In accordance with another embodiment, the present invention provides canagliflozin pyrazole co-crystal.

In accordance with another embodiment, the present invention provides a process for the preparation of Canagliflozin pyrazole co-crystal, comprising providing a solution or suspension comprising canagliflozin and pyrazole in one or more organic solvents and isolating the canagliflozin pyrazole co-crystal.

In accordance with another embodiment, the solid forms of canagliflozin of the present invention may be used as an intermediate in obtaining high purity canagliflozin, preferably amorphous form of canagliflozin.

In accordance with another embodiment, the present invention provides an improved process for the preparation of canagliflozin from the co-crystals of canagliflozin of the present invention.

In accordance with another embodiment, the present invention provides an improved process for the preparation of canagliflozin, comprising:
  a) preparing co-crystals of canagliflozin according to processes described as above; and
  b) converting the co-crystal of canagliflozin in to canagliflozin.

In accordance with another embodiment, the present invention provides an improved process for the preparation of canagliflozin; comprising:
  a) preparing co-crystal of canagliflozin according to processes described as above; and
  b) converting the co-crystal of canagliflozin in to canagliflozin; wherein the co-crystal former is selected from the group comprising DL-pipecolic acid, D-pipecolic acid, L-pipecolic acid, ammonia, nicotinic acid, isonicotinic acid, pyridine, pyrazole, pyrazine-2-carboxylic acid, imidazole, morpholine and the like.

In accordance with another embodiment, the present invention provides co-crystals of dapagliflozin.

In accordance with another embodiment, the present invention provides co-crystals of dapagliflozin and a co-crystal former, wherein the co-crystal former is selected from the group comprising DL-pipecolic acid, D-pipecolic acid, L-pipecolic acid, ammonia, nicotinic acid, isonicotinic acid, pyridine, pyrazole, pyrazine-2-carboxylic acid, imidazole, morpholine, and the like.

In accordance with another embodiment, the present invention provides a process for the preparation of co-crystals of dapagliflozin, comprising:
  a) providing a solution or suspension comprising dapagliflozin and a co-crystal former in one or more organic solvents; and
  b) isolating the co-crystals of dapagliflozin; wherein the co-crystal former is selected from the group comprising DL-pipecolic acid, D-pipecolic acid, L-pipecolic acid, ammonia, nicotinic acid, isonicotinic acid, pyridine, pyrazole, pyrazine-2-carboxylic acid, imidazole, morpholine, and the like.

In accordance with another embodiment, the present invention provides a process for the preparation of co-crystals of dapagliflozin, wherein the co-crystals are selected from the group comprising DL-pipecolic acid, D-pipecolic acid and L-pipecolic acid; comprising:
  a) providing a solution or suspension comprising dapagliflozin and a co-crystals former in one or more organic solvents; and
  b) isolating the co-crystals of dapagliflozin, wherein the co-crystals former is selected from the group comprising DL-pipecolic acid, D-pipecolic acid and L-pipecolic acid.

In accordance with another embodiment, the present invention provides co-crystals of dapagliflozin and a co-crystal former, wherein the co-crystal former is selected from the group comprising DL-pipecolic acid, D-pipecolic acid or L-pipecolic acid.

In accordance with another embodiment, the present invention provides dapagliflozin DL-pipecolic acid co-crystals.

In accordance with another embodiment, the present invention provides dapagliflozin DL-pipecolic acid co-crystals characterized by X-Ray powder diffraction (XRD) pattern substantially in accordance with FIG. 09.

In accordance with another embodiment, the present invention provides dapagliflozin DL-pipecolic acid co-crystals characterized by a $^1$H NMR Spectrum substantially in accordance with FIG. 10.

In accordance with another embodiment, the present invention provides dapagliflozin DL-pipecolic acid co-crystals characterized by a differential scanning calorimetry (DSC) thermogram substantially in accordance with FIG. 11.

In accordance with another embodiment, the present invention provides dapagliflozin DL-pipecolic acid co-crystals characterized by a thermogravimetric analysis (TGA) curve substantially in accordance with FIG. 12.

In accordance with another embodiment, the present invention provides dapagliflozin DL-pipecolic acid co-crystals characterized by one or more of the following: a powder X-Ray diffraction (XRD) pattern substantially in accordance with FIG. 09; a $^1$H NMR Spectrum substantially in accordance with FIG. 10; a differential scanning calorimetry (DSC) thermogram substantially in accordance with FIG. 11; and/or a thermogravimetric analysis (TGA) curve substantially in accordance with FIG. 12.

In accordance with another embodiment, the present invention provides a process for the preparation of dapagliflozin DL-pipecolic acid co-crystals, comprising providing a solution or suspension comprising dapagliflozin and DL-pipecolic acid in one or more organic solvents and isolating the dapagliflozin DL-pipecolic acid co-crystals.

In accordance with another embodiment, the present invention provides dapagliflozin D-pipecolic acid co-crystals.

In accordance with another embodiment, the present invention provides dapagliflozin D-pipecolic acid co-crystals characterized by X-Ray powder diffraction (XRD) pattern substantially in accordance with FIG. 13.

In accordance with another embodiment, the present invention provides a process for the preparation of dapagliflozin D-pipecolic acid co-crystals, comprising providing a solution or suspension comprising dapagliflozin and D-pipecolic acid in one or more organic solvents and isolating the dapagliflozin D-pipecolic acid co-crystals.

In accordance with another embodiment, the present invention provides dapagliflozin L-pipecolic acid co-crystals.

In accordance with another embodiment, the present invention provides dapagliflozin L-pipecolic acid co-crystals characterized by X-Ray powder diffraction (XRD) pattern substantially in accordance with FIG. 14.

In accordance with another embodiment, the present invention provides a process for the preparation of dapagliflozin L-pipecolic acid co-crystals, comprising providing a solution or suspension comprising dapagliflozin and L-pipecolic acid in one or more organic solvents and isolating the dapagliflozin L-pipecolic acid co-crystals.

In accordance with another embodiment, the present invention provides dapagliflozin 2,3-butanediol solvate.

In accordance with another embodiment, the present invention provides crystalline dapagliflozin 2,3-butanediol solvate.

In accordance with another embodiment, the present invention provides crystalline dapagliflozin 2,3-butanediol solvate characterized by X-Ray powder diffraction (XRD) pattern substantially in accordance with FIG. 15.

In accordance with another embodiment, the present invention provides crystalline dapagliflozin 2,3-butanediol solvate characterized by a $^1$H NMR Spectrum substantially in accordance with FIG. 16.

In accordance with another embodiment, the present invention provides crystalline dapagliflozin 2,3-butanediol solvate characterized by a differential scanning calorimetry (DSC) thermogram substantially in accordance with FIG. 17.

In accordance with another embodiment, the present invention provides crystalline dapagliflozin 2,3-butanediol solvate characterized by a thermogravimetric analysis (TGA) curve substantially in accordance with FIG. 18.

In accordance with another embodiment, the present invention provides dapagliflozin 2,3-butanediol solvate characterized by one or more of the following: a powder X-Ray diffraction (XRD) pattern substantially in accordance with FIG. 15; a $^1$H NMR Spectrum substantially in accordance with FIG. 16; a differential scanning calorimetry (DSC) thermogram substantially in accordance with FIG. 17; and/or a thermogravimetric analysis (TGA) curve substantially in accordance with FIG. 18.

In accordance with another embodiment, the present invention provides a process for the preparation of dapagliflozin 2,3-butanediol solvate, comprising:
   a) dissolving dapagliflozin or a solvate or a co-crystal in an organic solvent,
   b) treating the above solution with 2,3-butanediol,
   c) optionally adding seed crystals of dapagliflozin 2,3-butanediol solvate,
   d) adding an anti-solvent to the reaction mass, and
   e) isolating the dapagliflozin 2,3-butanediol solvate.

In accordance with another embodiment, the solid forms of dapagliflozin of the present invention may be used as an intermediate in obtaining high purity dapagliflozin, preferably amorphous form of dapagliflozin.

In accordance with another embodiment, the present invention provides a process for the preparation of amorphous form of dapagliflozin, wherein the process involves one or more solid forms of dapagliflozin of the invention as an intermediate.

In accordance with another embodiment, the present invention provides a process for the preparation of amorphous dapagliflozin, comprising:
   a) dissolving or suspending dapagliflozin co-crystals in a suitable solvent;
   b) optionally treating the step a) reaction mass with a suitable base or an acid;
   c) extracting dapagliflozin into an organic solvent; and
   d) removing the solvent to obtain amorphous form of dapagliflozin.

In accordance with another embodiment, the present invention provides a process for the preparation of amorphous dapagliflozin, comprising:
   a) dissolving or suspending dapagliflozin co-crystals in a suitable solvent,
   b) treating the step a) reaction mass with a suitable base or an acid,
   c) optionally extracting dapagliflozin into an organic solvent,
   d) removing the solvent to obtain a residue,
   e) dissolving the residue in an organic solvent to obtain a solution,
   f) adding an anti-solvent to the step e) solution or vice-versa,
   g) optionally seeding with amorphous dapagliflozin, and
   h) isolating the amorphous dapagliflozin.

In accordance with another embodiment, the present invention provides a process for the preparation of amorphous dapagliflozin, comprising:

a) providing a solution of dapagliflozin in a solvent selected from the group consisting of esters, ethers, alcohols, ketones, nitriles or mixtures thereof, and b) removing the solvent from the solution to obtain amorphous form of dapagliflozin.

In accordance with another embodiment, the present invention provides a process for the preparation of amorphous dapagliflozin, comprising:

a) providing a solution of dapagliflozin in a solvent selected from the group consisting of esters, ethers, alcohols, ketones, nitriles or mixtures thereof, b) adding an anti-solvent to the solution or vice versa, c) optionally seeding with amorphous dapagliflozin, and d) isolating the amorphous form of dapagliflozin; wherein the anti-solvent is selected from the group consisting of water, hydrocarbons solvents, ether solvents or mixtures thereof.

In accordance with another embodiment, the present invention provides co-crystals of empagliflozin.

In accordance with another embodiment, the present invention provides co-crystals of Empagliflozin and a co-crystal former, wherein the co-crystal former is selected from the group comprising DL-pipecolic acid, D-pipecolic acid, L-pipecolic acid, ammonia, nicotinic acid, isonicotinic acid, pyridine, pyrazole, pyrazine-2-carboxylic acid, imidazole, morpholine, proline and the like.

In accordance with another embodiment, the present invention provides a process for the preparation of co-crystals of empagliflozin, comprising:

a) providing a solution or suspension comprising empagliflozin and a co-crystal former, b) isolating the co-crystals of empagliflozin; wherein the co-crystal former is selected from the group comprising DL-pipecolic acid, D-pipecolic acid, L-pipecolic acid, ammonia, nicotinic acid, isonicotinic acid, pyridine, pyrazole, pyrazine-2-carboxylic acid, imidazole, morpholine, proline and the like.

In accordance with another embodiment, the present invention provides empagliflozin DL-pipecolic acid co-crystals.

In accordance with another embodiment, the present invention provides empagliflozin DL-pipecolic acid co-crystals hydrate.

In accordance with another embodiment, the present invention provides empagliflozin DL-pipecolic acid co-crystals characterized by X-Ray powder diffraction (XRD) pattern substantially in accordance with FIG. 21.

In accordance with another embodiment, the present invention provides empagliflozin DL-pipecolic acid co-crystals characterized by $^1$H NMR Spectrum substantially in accordance with FIG. 22.

In accordance with another embodiment, the present invention empagliflozin DL-pipecolic acid co-crystals characterized by a differential scanning calorimetry (DSC) thermogram substantially in accordance with FIG. 23.

In accordance with another embodiment, the present invention provides empagliflozin DL-pipecolic acid co-crystals characterized by a thermogravimetric analysis (TGA) curve substantially in accordance with FIG. 24.

In accordance with another embodiment, the present invention provides empagliflozin DL-pipecolic acid co-crystals characterized by one or more of the following: a powder X-Ray diffraction (XRD) pattern substantially in accordance with FIG. 21; a $^1$H NMR Spectrum substantially in accordance with FIG. 22; a differential scanning calorimetry (DSC) thermogram substantially in accordance with FIG. 23; and/or a thermogravimetric analysis (TGA) curve substantially in accordance with FIG. 24.

In accordance with another embodiment, the present invention provides a process for the preparation of empagliflozin DL-pipecolic acid co-crystals, comprising:

a) providing a solution or suspension comprising empagliflozin and DL-pipecolic acid, and b) isolating the empagliflozin DL-pipecolic acid co-crystals.

In accordance with another embodiment, the solid forms of co-crystals of empagliflozin of the present invention may be used as an intermediate in obtaining high purity empagliflozin.

In accordance with another embodiment, the present invention provides solid forms of SGLT2 inhibitors, which may have greater stability, bioavailability, and having desired pharmacological, pharmacokinetic and pharmacodynamic effects.

In accordance with another embodiment, the present invention provides a pharmaceutical composition comprising at least one of the solid forms of SGLT2 inhibitors described above and at least one or more pharmaceutically acceptable excipients.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
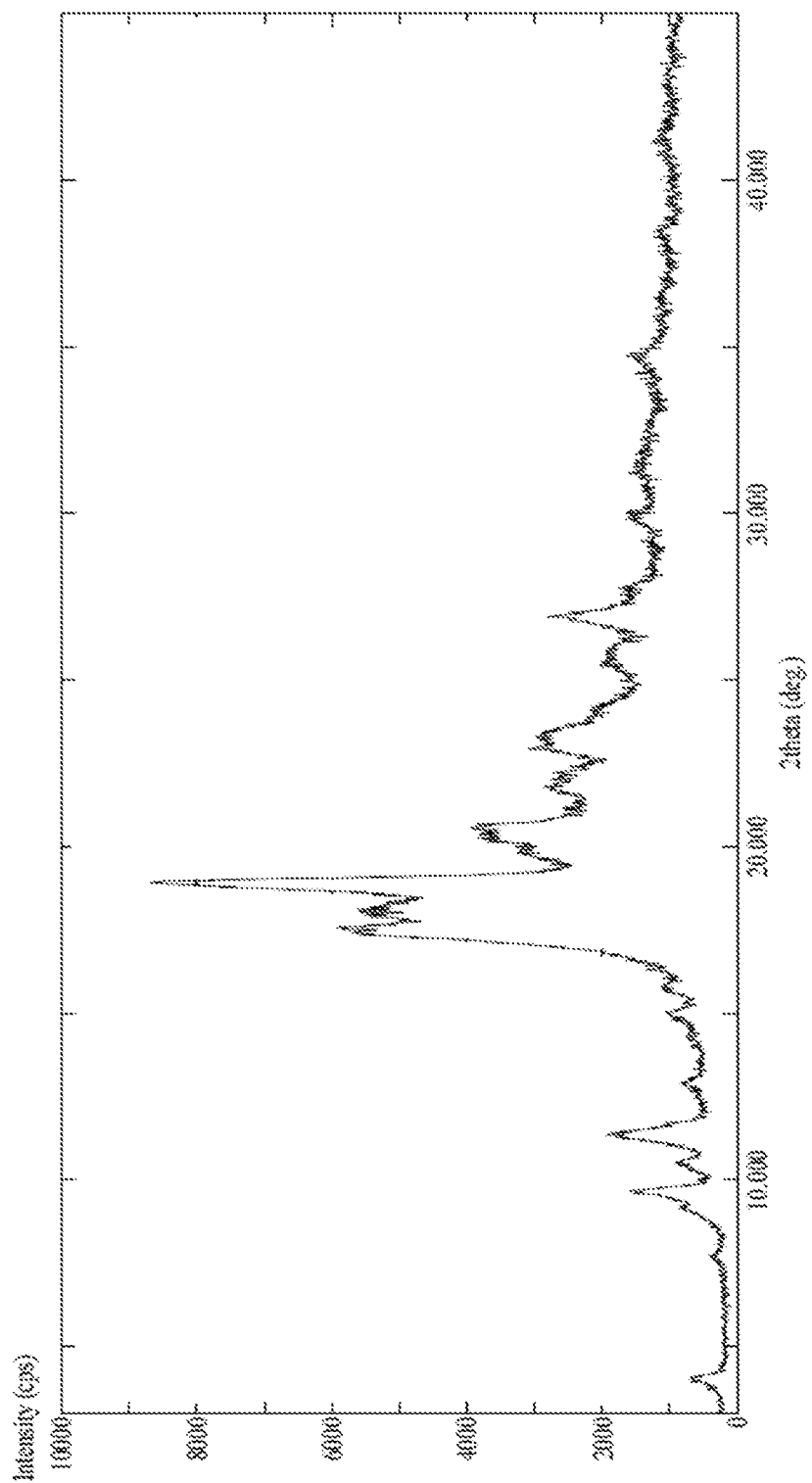
FIG. 1 is the characteristic powder XRD pattern of Canagliflozin DL-pipecolic acid co-crystal.

As used herein, the term "co-crystals" means a crystalline material comprised of two or more unique solids at room temperature, each containing distinctive physical characteristics, such as structure, melting point and heats of fusion.

As used herein, the term "solvate" refers to a crystalline compound in which molecules of solvents are incorporated into the crystal lattice of the compound.

The starting SGLT2 inhibitors used in the present invention is known in the art and can be prepared by any known methods, for example Canagliflozin may be synthesized as disclosed in U.S. Pat. Nos. 7,943,788 and 9,024,009; Dapagliflozin may be synthesized as disclosed in U.S. Pat. Nos. 6,515,117, 7,375,213, 7,932,379 and 7,919,598; and Empagliflozin may be synthesized as disclosed in U.S. Pat. No. 7,579,449, which are incorporated herein by reference; or the SGLT2 inhibitor may be obtained as a solution directly from a reaction mixture in which it is formed and used as such without isolation.

The present invention relates to solid forms of SGLT2 inhibitors, including their co-crystals, solvates and/or their polymorphs, processes for their preparation, pharmaceutical compositions containing the same and to their use in therapy.

In accordance with another embodiment, the present invention provides the solid forms of SGLT2 inhibitors exist in the form of co-crystals, solvates, polymorphs of co-crystals or polymorphs of solvates.

In particular, the present invention relates to solid forms of SGLT2 inhibitors, wherein the SGLT2 inhibitor can be, but is not limited to Canagliflozin, Dapagliflozin, Empagliflozin and the like, processes for their preparation and pharmaceutical compositions.

In accordance with one embodiment, the present invention provides novel co-crystals of SGLT2 inhibitors.

In accordance with another embodiment, the present invention provides co-crystals of SGLT2 inhibitors, wherein the SGLT2 inhibitor is selected from Canagliflozin, Dapagliflozin, Empagliflozin and the like.

In accordance with another embodiment, the present invention provides co-crystals of SGLT2 inhibitors and a co-crystal former, wherein the co-crystal former is selected from the group comprising DL-pipecolic acid, D-pipecolic acid, L-pipecolic acid, ammonia, nicotinic acid, isonicotinic acid, pyridine, pyrazole, pyrazine-2-carboxylic acid, imidazole, morpholine, proline and the like.

In accordance with another embodiment, the present invention provides co-crystals of SGLT2 inhibitors, wherein the SGLT2 inhibitor is selected from the group comprising Canagliflozin, Dapagliflozin, Empagliflozin and the like and co-crystal former is selected from the group comprising DL-pipecolic acid, D-pipecolic acid, L-pipecolic acid, ammonia, nicotinic acid, isonicotinic acid, pyridine, pyrazole, pyrazine-2-carboxylic acid, imidazole, morpholine, proline and the like.

The ratio of SGLT2 inhibitor to co-crystal former may be stoichiometric or non-stoichiometric according to the present invention. For example, 1:1, 1.5:1, 1:1.5, 2:1 and 1:2 ratios of SGLT2 inhibitor:co-crystal former is acceptable.

In accordance with another embodiment, the present invention provides co-crystals of SGLT2 inhibitors, which are characterized by one or more of analytical techniques such as powder X-Ray diffraction (XRD); $^1$H NMR Spectrum; infrared spectrum (IR), differential scanning calorimetry (DSC) and/or thermogravimetric analysis (TGA), among others.

In accordance with another embodiment, the present invention provides a process for the preparation of co-crystals of SGLT2 inhibitors, comprising:
 a) providing a solution or suspension comprising SGLT2 inhibitor and a co-crystal former in one or more solvents; and
 b) isolating the co-crystals of SGLT2 inhibitors; wherein the SGLT2 inhibitor is selected from the group comprising Canagliflozin, Dapagliflozin and Empagliflozin and wherein the co-crystal former is selected from the group comprising DL-pipecolic acid, D-pipecolic acid, L-pipecolic acid, ammonia, nicotinic acid, isonicotinic acid, pyridine, pyrazole, pyrazine-2-carboxylic acid, imidazole, morpholine, proline and the like.

The step of providing a solution or suspension includes any form of SGLT2 inhibitor that may be combined with one or more organic solvents at a suitable temperature, and then the co-crystal former may be mixed with the resulting solution or slurry. Alternatively, the mixture may be formed by adding both the SGLT2 inhibitor and the co-crystal former at the same time in to one or more organic solvents.

Suitable one or more solvents includes but are not limited to alcohols, esters, ethers, ketones, nitriles, halogenated hydrocarbons, aromatic hydrocarbons, aliphatic hydrocarbons, amides, nitroalkanes and the like; water and mixtures thereof.

The alcohols include, but are not limited to methanol, ethanol, isopropanol, n-propanol, n-butanol, isobutanol and the like; esters include, but are not limited to methyl acetate, ethyl acetate, isopropyl acetate and the like; ethers include, but are not limited to tetrahydrofuran, dimethyl ether, diisopropyl ether, methyl tertiary butyl ether, 1,4-dioxane and the like; ketones include, but are not limited to acetone, methyl isobutyl ketone, methyl ethyl ketone and the like; nitriles include, but are not limited to acetonitrile, propionitrile and the like; halogenated hydrocarbons include, but are not limited to methylene chloride, ethylene chloride, chloroform, carbon tetrachloride and the like; aromatic hydrocarbons include, but are not limited to toluene, xylene and the like; aliphatic hydrocarbons include, but are not limited to n-hexane, n-heptane, cyclohexane and the like; amides include, but are not limited to dimethyl formamide, dimethyl acetamide, dimethyl sulfoxide, N-methyl pyrrolidinone and the like; nitroalkanes include, but are not limited to nitromethane, nitroethane and the like and mixtures thereof. Preferably the one or more solvents include methanol, ethanol, n-butanol, ethyl acetate, isopropyl acetate, hexane, heptane and mixtures thereof; more preferably ethanol, n-butanol, ethyl acetate, isopropyl acetate, heptane and mixtures thereof and optionally a mixture of these solvents with water.

The temperature suitable for dissolving or suspending the SGLT2 inhibitor in the one or more organic solvents depends on the solvent used and the amount of SGLT2 inhibitor in the reaction mass. Typically, the solution or suspension is heated at a temperature of at least about 30° C. to about reflux.

In step b) of the foregoing process, the isolation of co-crystals of SGLT2 inhibitors may be carried out by crystallization, solvent precipitation, concentration by subjecting the solution to heating, spray drying, freeze drying, evaporation on rotary evaporator under vacuum, agitated thin film evaporator (ATFE) and the like. Preferably, the reaction may be cooled to a temperature from about 35° C. or less and then an antisolvent such as n-heptane is added and then optionally the reaction medium can be heated to about 40° C. to about 75° and followed by cooling the suspension to less than about 30° C. The precipitated product can be recovered by conventional techniques, for example filtration.

The obtained co-crystal of SGLT2 inhibitor, if required, is further purified by heating the co-crystal of SGLT2 inhibitor in a suitable organic solvent selected from the group consisting of alcohols, esters, ketones, ethers, halogenated solvents, hydrocarbons, nitriles, carbonates, nitro alkanes, glycols, water or mixtures thereof.

Examples of suitable organic solvent for purifying co-crystals of the present invention include but are not limited to alcohols such as methanol, ethanol, isopropanol, n-butanol, sec-butanol, tert-butanol, and the like; esters such as ethyl acetate, isopropyl acetate, n-butyl acetate, isobutyl acetate, tert-butyl acetate and the like; ketones such as acetone, methyl isobutyl ketone, 2-pentanone, cyclopentanone, cyclohexanone and the like; ethers such as diisopropyl ether, di tert-butyl ether, ethyl tert-butyl ether, and the like; halogenated solvents such as dichloromethane, 1-chlorobutane, and the like; hydrocarbons such as hexane, heptane, pentane, cyclohexane, methyl cyclohexane, and the like; nitriles such as acetonitrile, propionitrile, butyronitrile, benzonitrile and the like; carbonates such as diethyl carbonate, propylene carbonate, dibenzyl carbonate and the like; nitro alkanes such as nitromethane, nitroethane and the like; glycols such as ethylene glycol, propylene glycol and the like; water or mixtures thereof. Preferably the suitable organic solvent includes methanol, ethanol, isopropyl acetate, ethyl acetate, acetone and mixtures thereof; more preferably ethanol, ethyl acetate and mixtures thereof.

The mixture of co-crystal of SGLT2 inhibitor and the suitable organic solvent may be heated to dissolve all solids in to solvent at a temperature of about 30° C. to reflux. Then the resultant solution may optionally be cooled to less than 30° C. and the precipitated solid can be isolated by conventional techniques known in the art, for example, filtration. The resultant co-crystals of SGLT2 inhibitors may optionally be further dried. Drying can be suitably carried out in a tray dryer, vacuum oven, air oven, fluidized bed drier, spin flash dryer, flash dryer and the like. The drying can be carried out at a temperature ranging from about 40° C. to about 100° C.

In another embodiment, the present invention provides co-crystals of SGLT2 inhibitors having a chemical purity greater than or equal to about 97%, as measured by HPLC, preferably about 98% as measured by HPLC, and more preferably about 99.5%, as measured by HPLC.

In another embodiment, the co-crystals of the present invention are obtained in substantially pure form.

Furthermore, some of the co-crystals of the present invention may exist as polymorphs and as such are intended to be included in the present invention. In addition, some of the co-crystals of the present invention may form solvates with water (i.e., hydrates) or common organic solvents, and such solvates are also intended to be encompassed within the scope of this invention.

In another embodiment, the present invention provides co-crystals of SGLT2 inhibitors, wherein the SGLT2 inhibitor is Canagliflozin.

In another embodiment, the present invention provides co-crystals of Canagliflozin and a co-crystal former, wherein the co-crystal former is selected from the group comprising DL-pipecolic acid, D-pipecolic acid, L-pipecolic acid, ammonia, nicotinic acid, isonicotinic acid, pyridine, pyrazole, pyrazine-2-carboxylic acid, imidazole, morpholine and the like.

In another embodiment, the present invention provides co-crystals of canagliflozin and a co-crystal former, wherein the co-crystal former is selected from the group comprising DL-pipecolic acid, D-pipecolic acid, L-pipecolic acid, nicotinic acid, pyrazine 2-carboxylic acid, ammonia or pyrazole.

In another embodiment, the present invention provides Canagliflozin DL-pipecolic acid co-crystals.

In another embodiment, the present invention provides a process for the preparation of Canagliflozin DL-pipecolic acid co-crystals, comprising providing a solution or suspension comprising Canagliflozin and DL-pipecolic acid in one or more organic solvents and isolating the Canagliflozin DL-pipecolic acid co-crystal.

Examples of one or more organic solvents used herein in the foregoing process includes but are not limited to alcohols such as methanol, ethanol, n-propanol, isopropanol, n-butanol, iso-butanol and the like; ketones such as acetone, methyl isobutyl ketone, methyl ethyl ketone and the like; ethers such as tetrahydrofuran, 2-methyl tetrahydrofuran, diethyl ether, methyl tertiary butyl ether, 1,4-dioxane and the like; aliphatic hydrocarbons such as hexane, heptane, pentane and the like; aromatic hydrocarbons such as toluene, xylene and the like; halogenated hydrocarbons such as dichloromethane, chloroform and the like; nitriles such as acetonitrile, propionitrile, benzonitrile and the like or mixtures thereof. Preferably the one or more organic solvents include methanol, ethanol, n-butanol, ethyl acetate, isopropyl acetate, hexane, heptane and mixtures thereof; more preferably ethanol, n-butanol, ethyl acetate, isopropyl acetate, heptane and mixtures thereof and optionally a mixture of these solvents with water.

The step of providing a solution or suspension comprising Canagliflozin and DL-pipecolic acid in organic solvent may include heating to dissolve Canagliflozin and DL-pipecolic acid in the organic solvent. The temperature suitable for dissolving or suspending the Canagliflozin and DL-pipecolic acid in the organic solvent depends on the solvent used and the amount of Canagliflozin and DL-pipecolic acid in the solution. Typically, it is heated at a temperature of at least about 30° C. to about reflux. Preferably, the solution is heated at about 30° C. to about 80° C.

Isolation of the Canagliflozin DL-pipecolic acid co-crystal obtained may be carried out by optionally allowing the reaction mass to gradually cool to a temperature of less than 30° C. and the Canagliflozin DL-pipecolic acid co-crystal can be isolated by conventional techniques, for example by filtration.

The obtained Canagliflozin DL-pipecolic acid co-crystal, if required, is further purified by heating the co-crystal of SGLT2 inhibitor in a suitable organic solvent selected from the group consisting of alcohols, esters, ketones, ethers, halogenated solvents, hydrocarbons, nitriles, carbonates, alkyl nitrates, glycols, water or mixtures thereof.

Examples of suitable organic solvent for purifying Canagliflozin DL-pipecolic acid co-crystal is represented as solvents mentioned just as above for the purification step of SGL2 inhibitors. Preferably the suitable organic solvent for purification of Canagliflozin DL-pipecolic acid co-crystal includes methanol, ethanol, isopropyl acetate, ethyl acetate, acetone and mixtures thereof; more preferably ethanol, ethyl acetate and mixtures thereof.

The mixture of Canagliflozin DL-pipecolic acid co-crystal and the suitable organic solvent may be heated to dissolve all solids in to solvent at a temperature of about 30° C. to reflux. Then the resultant solution may optionally be cooled to less than 30° C. and the precipitated solid can be isolated by conventional techniques known in the art, for example, filtration. The resultant Canagliflozin DL-pipecolic acid co-crystal may optionally be further dried. Drying can be suitably carried out in a tray dryer, vacuum oven, air oven, fluidized bed drier, spin flash dryer, flash dryer and the like. The drying can be carried out at a temperature ranging from about 40° C. to about 100° C., preferably from about 50° C. to about 80° C.

In another embodiment, Canagliflozin DL-pipecolic acid co-crystal recovered using the process as described just above is substantially a crystalline form.

In another embodiment, the present invention provides Canagliflozin DL-pipecolic acid co-crystal characterized by X-Ray powder diffraction (XRD) pattern substantially in accordance with FIG. 01.

In another embodiment, the present invention provides Canagliflozin DL-pipecolic acid co-crystal characterized by X-Ray powder diffraction (XRD) pattern having one or more peaks at about 4.00, 9.12, 9.60, 10.50, 11.34, 14.92, 17.56, 17.92, 18.92, 19.80, 20.18, 20.60, 21.74, 22.20, 22.94, 23.48 and 26.90±0.2° 2θ.

Figure 2:
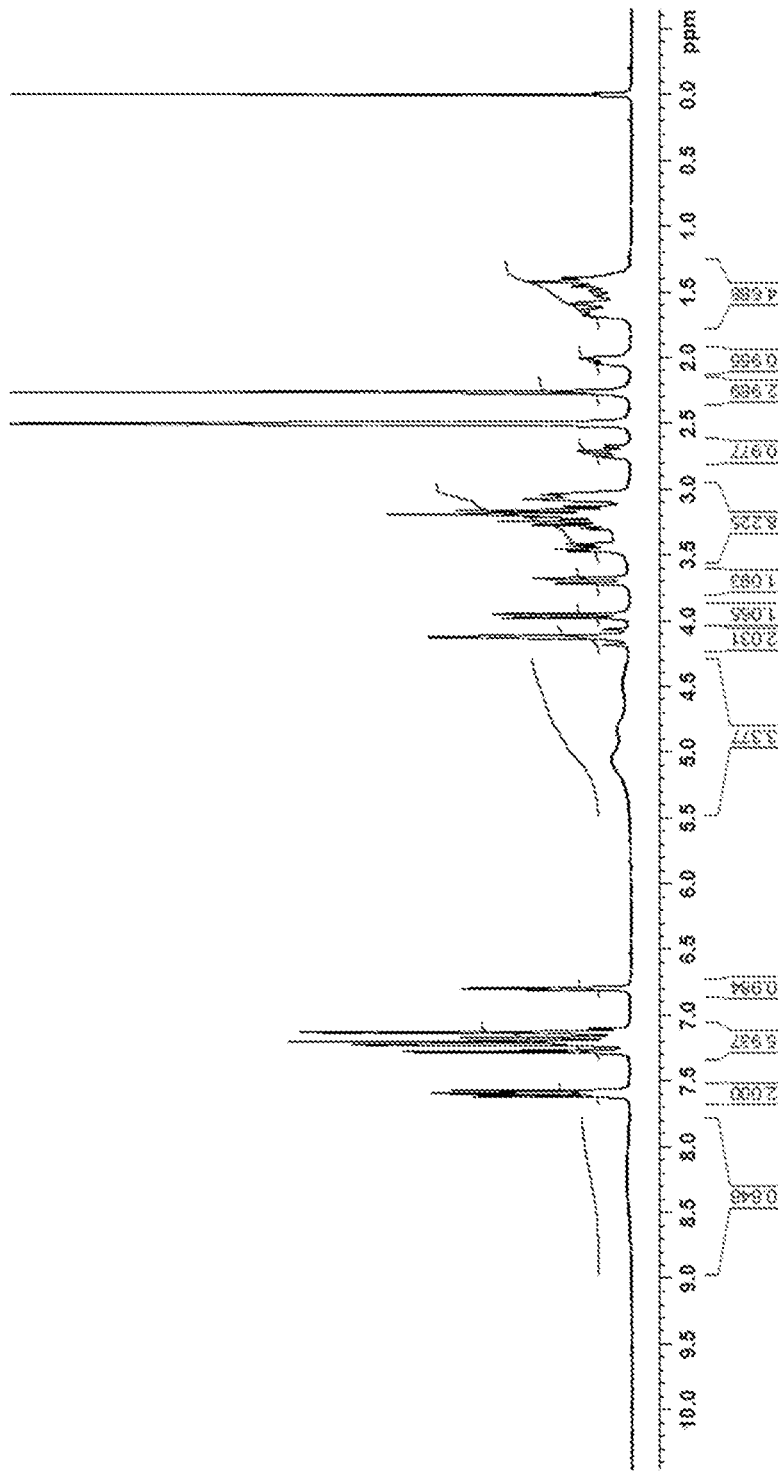
FIG. 2 is the characteristic $^1$H NMR Spectrum of Canagliflozin DL-pipecolic acid co-crystal.

In another embodiment, the present invention provides Canagliflozin DL-pipecolic acid co-crystal characterized by a $^1$H NMR Spectrum substantially in accordance with FIG. 02.

Figure 3:
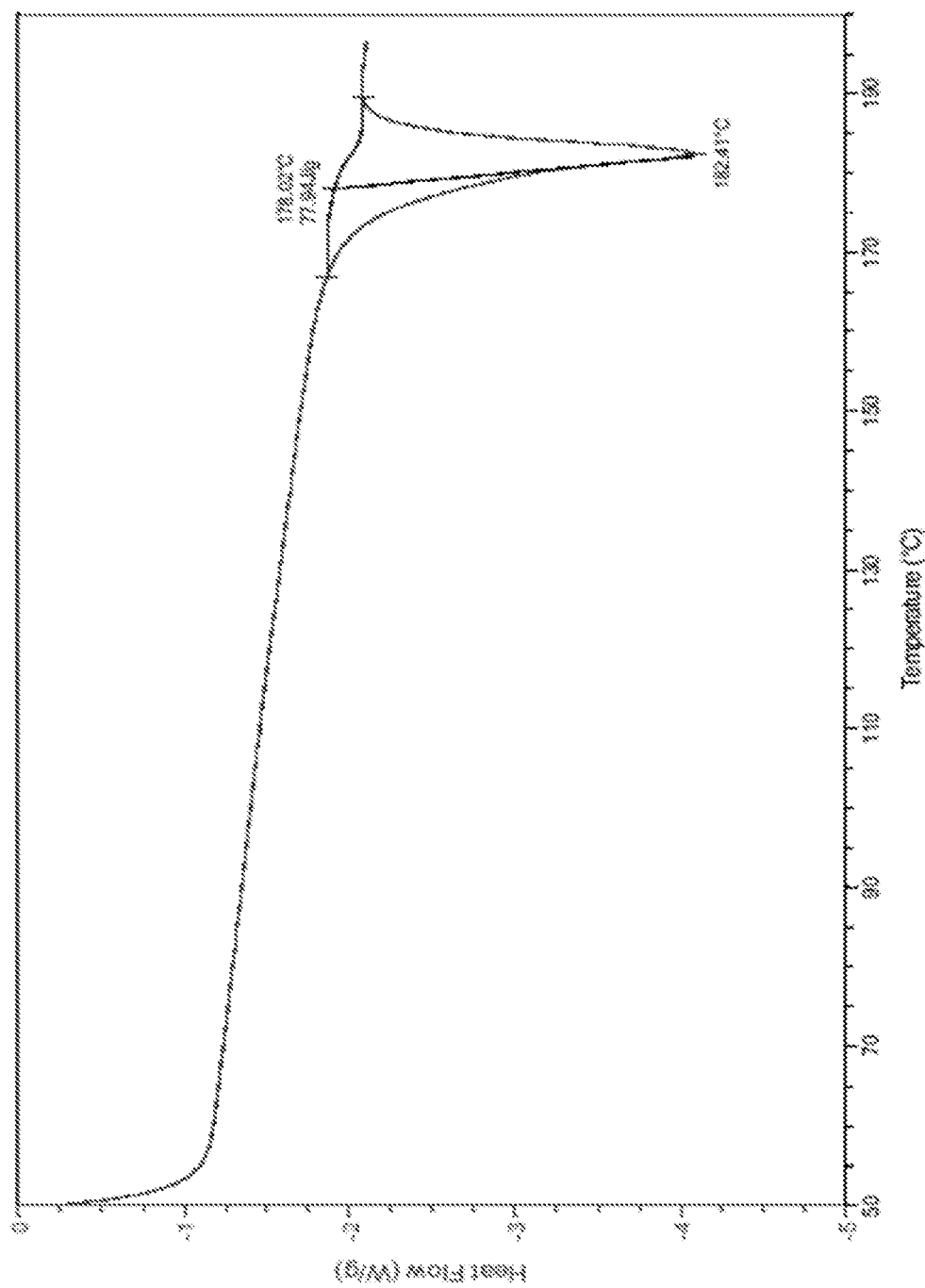
FIG. 3 is the characteristic DSC thermogram of Canagliflozin DL-pipecolic acid co-crystal.

In another embodiment, the present invention provides Canagliflozin DL-pipecolic acid co-crystal characterized by a differential scanning calorimetry (DSC) thermogram substantially in accordance with FIG. 03.

Figure 4:
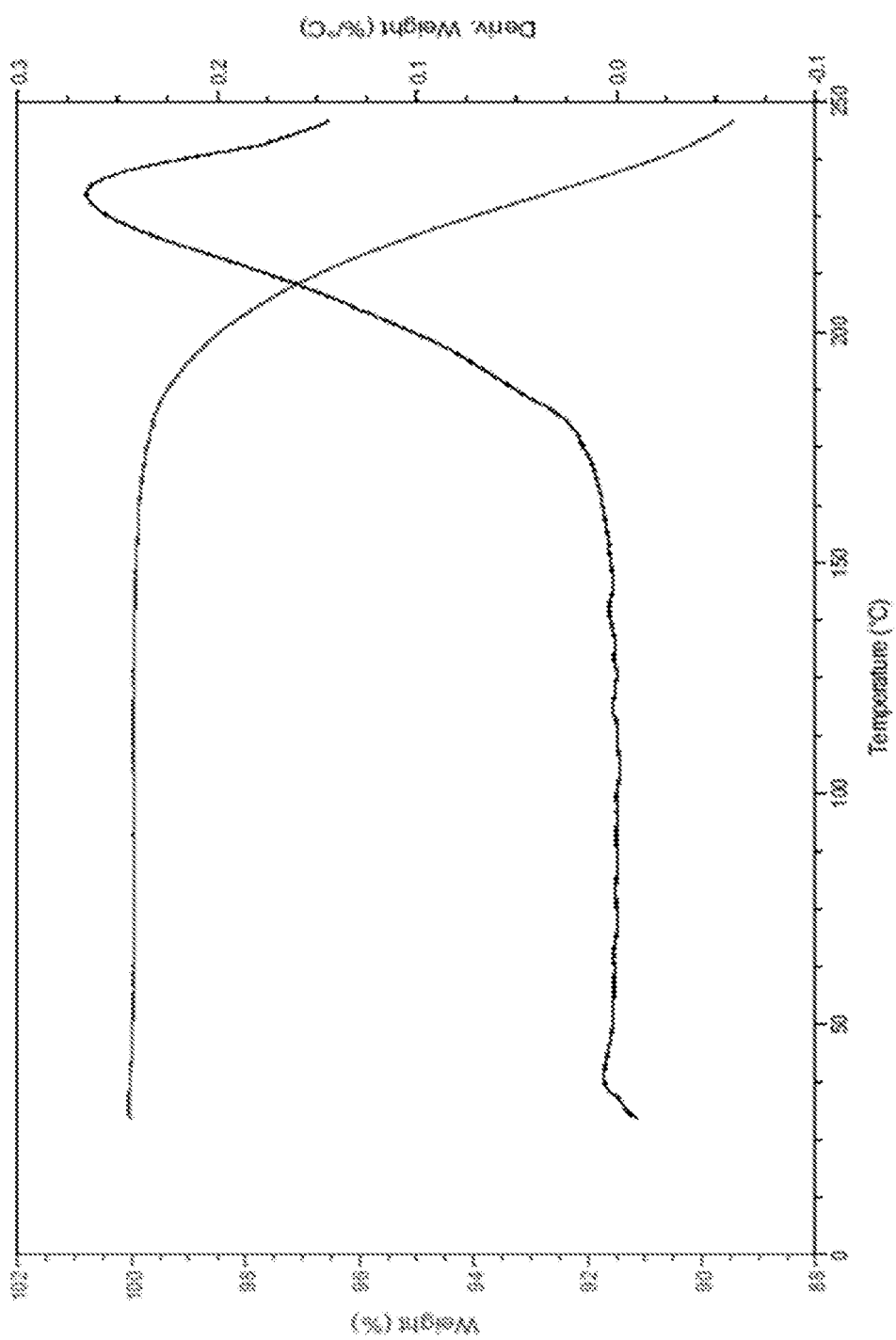
FIG. 4 is the characteristic TGA curve of Canagliflozin DL-pipecolic acid co-crystal.

In another embodiment, the present invention provides Canagliflozin DL-pipecolic acid co-crystal characterized by a thermogravimetric analysis (TGA) curve substantially in accordance with FIG. 04.

Figure 5:
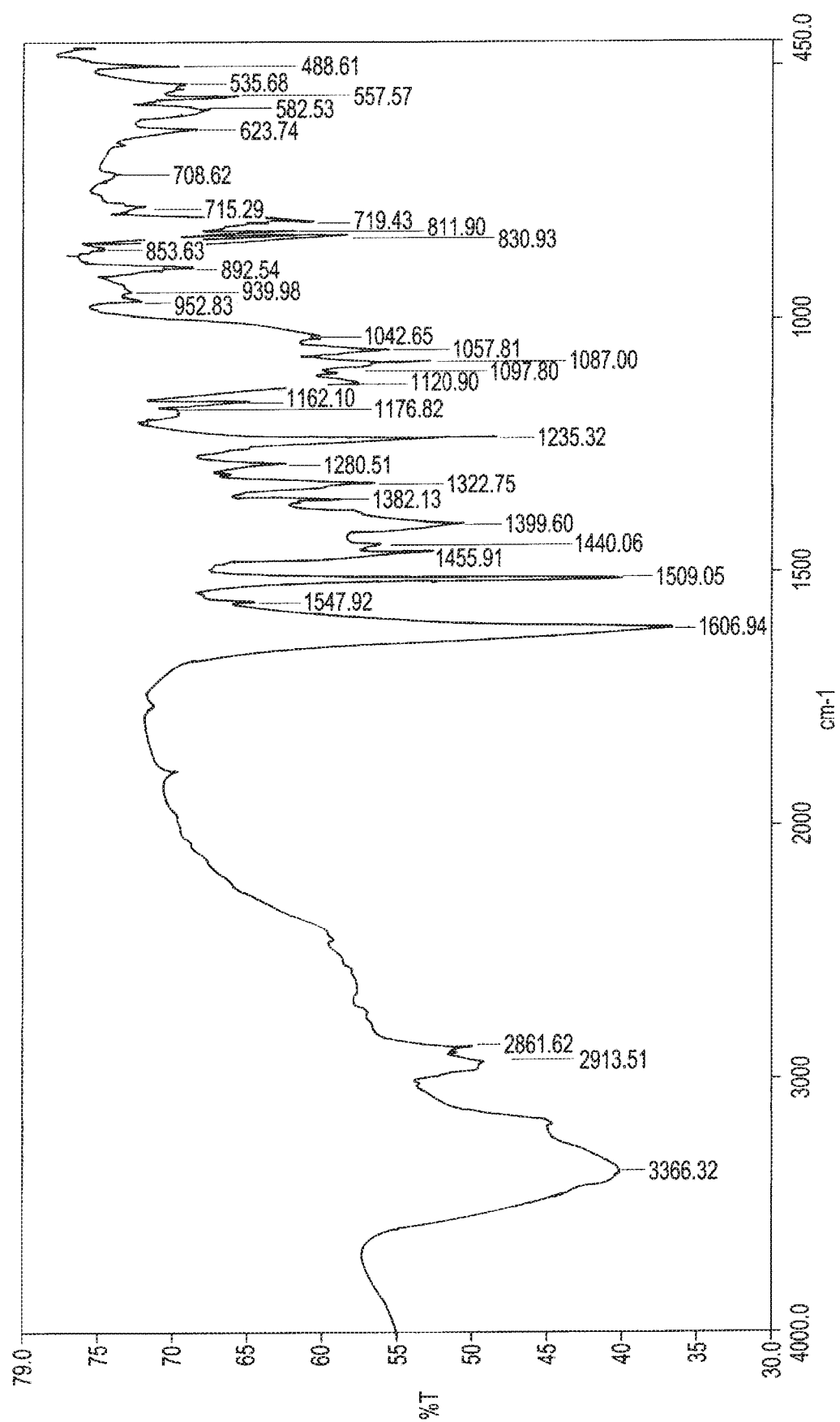
FIG. 5 is the characteristic IR spectrum of Canagliflozin DL-pipecolic acid co-crystal.

In another embodiment, the present invention provides Canagliflozin DL-pipecolic acid co-crystal characterized by an Infrared spectroscopy (IR) spectrum substantially in accordance with FIG. 05.

In another embodiment, the present invention provides Canagliflozin DL-pipecolic acid co-crystal characterized by one or more of the following: a powder X-Ray diffraction (XRD) pattern substantially in accordance with FIG. 01; a $^1$H NMR Spectrum substantially in accordance with FIG. 02; a differential scanning calorimetry (DSC) thermogram substantially in accordance with FIG. 03; a thermogravimetric analysis (TGA) curve substantially in accordance with FIG. 04 and/or an Infrared spectroscopy (IR) spectra substantially in accordance with FIG. 05.

In another embodiment, the present invention provides canagliflozin L-pipecolic acid co-crystal.

In another embodiment, the present invention provides a process for the preparation of Canagliflozin L-pipecolic acid co-crystal, comprising providing a solution or suspension comprising canagliflozin and L-pipecolic acid in one or more organic solvents and isolating the canagliflozin L-pipecolic acid co-crystal.

The aforementioned process for the preparation of canagliflozin L-pipecolic acid co-crystal includes dissolving canagliflozin and L-pipecolic acid in one or more organic solvents as herein before defined; preferably ethanol, ethyl acetate and mixtures thereof at a suitable temperature, for example at about 30° C. to about reflux temperature, preferably at about 50° C. to reflux. Then cooling the reaction mixture to less than 60° C. and then optionally an antisolvent such as n-heptane may be added to precipitation of the resultant product or directly cooling the reaction solution to precipitation. The precipitated Canagliflozin L-pipecolic acid co-crystal can be recovered by conventional techniques, for example filtration.

Optionally, the resultant Canagliflozin L-pipecolic acid co-crystals may be purified using a suitable solvent system. Preferable solvent includes, but are not limited to ethanol, ethyl acetate and mixtures thereof. The mixture of Canagliflozin L-pipecolic acid co-crystal and the suitable organic solvent may be heated to dissolve all solids in to solvent at a temperature of about 30° C. to reflux. Then the resultant solution may optionally be cooled to less than 30° C. and the precipitated solid can be isolated by conventional techniques known in the art, for example, filtration followed by optionally dried.

In another embodiment, the present invention provides canagliflozin D-pipecolic acid co-crystal.

In another embodiment, the present invention provides a process for the preparation of Canagliflozin D-pipecolic acid co-crystal, comprising providing a solution or suspension comprising canagliflozin and D-pipecolic acid in one or more organic solvents and isolating the canagliflozin D-pipecolic acid co-crystal.

The aforementioned process for the preparation of canagliflozin D-pipecolic acid co-crystal includes dissolving canagliflozin and D-pipecolic acid in one or more organic solvents as herein before defined; preferably ethanol, ethyl acetate and mixtures thereof at a suitable temperature, for example at about 30° C. to about reflux temperature, preferably at about 50° C. to reflux. Then cooling the reaction mixture to less than 60° C. and then optionally an antisolvent such as n-heptane may be added to precipitation of the resultant product or directly cooling the reaction solution to precipitation. The precipitated Canagliflozin D-pipecolic acid co-crystal can be recovered by conventional techniques, for example filtration.

Optionally, the resultant Canagliflozin D-pipecolic acid co-crystals may be purified using a suitable solvent system. Preferable solvent includes, but are not limited to ethanol, ethyl acetate and mixtures thereof. The mixture of Canagliflozin D-pipecolic acid co-crystal and the suitable organic solvent may be heated to dissolve all solids in to solvent at a temperature of about 30° C. to reflux. Then the resultant solution may optionally be cooled to less than 30° C. and the precipitated solid can be isolated by conventional techniques known in the art, for example, filtration followed by optionally dried.

In another embodiment, the present invention provides canagliflozin nicotinic acid co-crystal.

In another embodiment, the present invention provides a process for the preparation of Canagliflozin nicotinic acid co-crystal, comprising providing a solution or suspension comprising canagliflozin and nicotinic acid in one or more organic solvents and isolating the canagliflozin nicotinic acid co-crystal.

The above mentioned process for the preparation of canagliflozin nicotinic acid co-crystal includes dissolving canagliflozin and nicotinic acid in one or more organic solvents as herein before defined; preferably in ethanol at a suitable temperature, for example at about 30° C. to about reflux temperature, preferably at about 50° C. to about reflux temperature. Then cooling the reaction mixture to less than about 30° C. and isolating the resulting Canagliflozin nicotinic acid co-crystal by conventional techniques, for example by filtration.

In another embodiment, the present invention provides canagliflozin pyrazine-2-carboxylic acid co-crystal.

In another embodiment, the present invention provides a process for the preparation of Canagliflozin pyrazine-2-carboxylic acid co-crystal, comprising providing a solution or suspension comprising canagliflozin and pyrazine-2-carboxylic acid in one or more organic solvents and isolating the canagliflozin pyrazine-2-carboxylic acid co-crystal.

The above mentioned process for the preparation of canagliflozin pyrazine-2-carboxylic acid co-crystal includes dissolving canagliflozin and pyrazine-2-carboxylic acid in one or more organic solvents as herein before defined; preferably in ethanol at a suitable temperature, for example at about 30° C. to about reflux temperature, preferably at about 50° C. to about reflux temperature. Then cooling the reaction mixture to room temperature and isolating the resulting Canagliflozin pyrazine-2-carboxylic acid co-crystal by conventional techniques, for example by filtration.

In another embodiment, the present invention provides canagliflozin pyrazole co-crystal.

In another embodiment, the present invention provides a process for the preparation of Canagliflozin pyrazole co-crystal, comprising providing a solution or suspension comprising canagliflozin and pyrazole in one or more organic solvents and isolating the canagliflozin pyrazole co-crystal.

The foregoing process for the preparation of canagliflozin pyrazole co-crystal includes dissolving canagliflozin and pyrazole in one or more organic solvents as herein before defined, preferably in ethanol, at a suitable temperature, for example at about 30° C. to about reflux temperature, preferably at about 50° C. to about reflux temperature. Then cooling the reaction mixture to less than 60° C. and then optionally an antisolvent such as n-heptane may be added to precipitation of the resultant product. The precipitated Canagliflozin pyrazole co-crystals can be recovered by conventional techniques, for example filtration.

In another embodiment, preparation of the co-crystals of the present invention significantly reduces the formation of unwanted alpha isomer thereby substantially pure beta isomer is resulted.

In another embodiment, the co-crystals of canagliflozin of the present invention may be used as an intermediate in obtaining high purity canagliflozin.

In another embodiment, the present invention provides an improved process for the preparation of canagliflozin from the co-crystals of canagliflozin.

In another embodiment, the present invention provides an improved process for the preparation of canagliflozin from the Canagliflozin DL-pipecolic acid co-crystal as an intermediate.

In another embodiment, the present invention provides an improved process for the preparation of canagliflozin; comprising:
 a) preparing co-crystal of canagliflozin according to processes described as above; and
 b) converting the co-crystal of canagliflozin in to canagliflozin; wherein the co-crystal former is selected from the group comprising DL-pipecolic acid, D-pipecolic acid, L-pipecolic acid, ammonia, nicotinic acid, isonicotinic acid, pyridine, pyrazole, pyrazine-2-carboxylic acid, imidazole, morpholine and the like.

The co-crystals of canagliflozin, for instance Canagliflozin DL-pipecolic acid co-crystal prepared by the process as described above, are dissolved in the one or more organic solvents. Examples of one or more organic solvents used herein includes but are not limited to alcohols such as methanol, ethanol, n-propanol, isopropanol, n-butanol, isobutanol and the like; ketones such as acetone, methyl isobutyl ketone, methyl ethyl ketone and the like; esters such as ethyl acetate, isopropyl acetate, isobutyl acetate and the like; ethers such as tetrahydrofuran, 2-methyl tetrahydrofuran, diethyl ether, methyl tertiary butyl ether, 1,4-dioxane and the like; aliphatic hydrocarbons such as hexane, heptane, pentane and the like; aromatic hydrocarbons such as toluene, xylene and the like; halogenated hydrocarbons such as dichloromethane, chloroform and the like; nitriles such as acetonitrile, propionitrile, benzonitrile and the like or mixtures thereof. Preferable solvent is ethyl acetate, isopropyl acetate, dichloromethane, toluene, methyl tertiary butyl ether and mixtures thereof.

The temperature suitable for dissolving the Canagliflozin DL-pipecolic acid co-crystal in the one or more solvents depends on the solvent used and the amount of Canagliflozin DL-pipecolic acid co-crystal in the solution. Typically, the temperature for dissolving Canagliflozin DL-pipecolic acid co-crystal in an organic solvent is at least about 25° C. to about reflux.

Then a suitable base may be added from about 0.5 to about 5 mole equivalents per mole of starting Canagliflozin DL-pipecolic acid co-crystal, preferably about 1 to about 4 moles.

Suitable base is either inorganic or organic base. The inorganic base used herein is selected from the group comprising of alkali metal carbonates such as sodium carbonate, potassium carbonate, cesium carbonate; alkali metal bicarbonates such as sodium bicarbonate, potassium bicarbonate and the like; alkali metal hydroxides such as sodium hydroxide, potassium hydroxide and lithium hydroxide and the like; alkali metal hydride such as sodium hydride, potassium hydride and the like. The organic base used herein is selected from the group comprising of alkyl amines such as di-isopropyl ethylamine, triethyl amine and the like; heterocyclic amines such as pyridine and the like. Preferably the base used herein is sodium bicarbonate, more preferably an aqueous solution of sodium bicarbonate.

Isolation of canagliflozin may be carried out by known methods such as concentrating the solvent from the solution by evaporation under spray drying, agitated thin film dryer, under normal or atmospheric pressure; cooling the solution to precipitation and the like. Preferably isolation of canagliflozin can be carried out by separating the product containing organic layer and concentrating it completely under vacuum to obtain a residue. The canagliflozin product from the residue so obtained can be recovered using a suitable solvent.

The suitable solvent useful in the isolation of canagliflozin comprises of aromatic hydrocarbons such as toluene, xylene and the like; aliphatic hydrocarbons such as heptane, hexane, cyclohexane, cycloheptane, methyl cyclohexane and the like; ethers such as methyl tertiary butyl ether, di-isopropyl ether, di-ethyl ether, tetrahydrofuran; ketones such as acetone, methyl ethyl ketone, methyl isobutyl ketone and the like. Preferably the suitable solvent used herein is cyclohexane and the crystallization can be carried out by mixing the residue obtained from the above in cyclohexane at a temperature of about 25° C. to reflux temperature, preferably at about 25° C. to about 35° C. The resultant canagliflozin can be isolated by conventional techniques known in the art, for example filtration.

The resultant canagliflozin may optionally be further dried. Drying can be suitably carried out in a tray dryer, vacuum oven, air oven, fluidized bed drier, spin flash dryer, flash dryer and the like. The drying can be carried out at a temperature ranging from about 30° C. to about 80° C. for a time period ranging from about 1 hour to about 12 hours.

In another embodiment, canagliflozin obtained according to the present invention is in substantially pure form.

In another embodiment, canagliflozin obtained according to the present invention is in substantially amorphous form.

In another embodiment, the present invention provides Canagliflozin having a chemical purity greater than or equal to about 97%, as measured by HPLC, preferably about 98% as measured by HPLC, and more preferably about 99.5%, as measured by HPLC and substantially free of alpha isomer impurity.

As used herein, the term "substantially free" refers to Canagliflozin having less than 2% as measured by HPLC of alpha isomer impurity; preferably less than 1% of alpha isomer impurity as measured by HPLC, more preferably less than about 0.5% of alpha isomer impurity as measured by HPLC.

In another embodiment, the present invention provides co-crystals of dapagliflozin.

In another embodiment, the present invention provides co-crystals of dapagliflozin, wherein the co-crystal former is selected from the group comprising DL-pipecolic acid, D-pipecolic acid, L-pipecolic acid, ammonia, nicotinic acid, isonicotinic acid, pyridine, pyrazole, pyrazine-2-carboxylic acid, imidazole, morpholine and the like.

In another embodiment, the present invention provides a process for the preparation of co-crystals of dapagliflozin, comprising:
  a) providing a solution or suspension comprising dapagliflozin and a co-crystal former in one or more solvents; and
  b) isolating the co-crystals of dapagliflozin; wherein the co-crystals former is selected from the group comprising DL-pipecolic acid, D-pipecolic acid, L-pipecolic acid, ammonia, nicotinic acid, isonicotinic acid, pyridine, pyrazole, pyrazine-2-carboxylic acid, imidazole, morpholine and the like.

The step of providing a solution or suspension includes any form of dapagliflozin that may be mixed with one or more solvents and co-crystals former or includes any form of dapagliflozin that may be combined with one or more solvents and then the co-crystals former may be mixed with the resulting solution or slurry. Alternatively, the mixture may be formed by adding dapagliflozin and co-crystals former at the same time in to one or more organic solvents.

Examples of one or more solvents of step a) includes but are not limited to esters such as methyl acetate, ethyl acetate, isopropyl acetate, n-propyl acetate, n-butyl acetate, t-butyl acetate and the like; alcohols such as methanol, ethanol, isopropanol, n-propanol, n-butanol, isobutanol and the like; ethers such as tetrahydrofuran, dimethyl ether, diisopropyl ether, methyl tertiary butyl ether, 1,4-dioxane and the like, ketones such as acetone, methyl ethyl ketone, methyl isobutyl ketone and the like, cyclic hydrocarbon solvents such as hexane, heptane, cyclohexane and the like, halogenated hydrocarbon solvents such as dichloromethane, dichloroethane, chloroform and the like, nitriles such as acetonitrile, propionitrile and the like; water or mixtures thereof; preferably isopropyl acetate, ethanol, isopropanol; water or mixture thereof.

The temperature suitable for dissolving or suspending the dapagliflozin in one or more organic solvents depends on the solvent used and the amount of dapagliflozin in the reaction mass. Typically, the solution or suspension is heated at a temperature of at least about 30° C. to about reflux.

The step b) of the foregoing process, the isolation of co-crystals of dapagliflozin may be carried out by concentration, by subjecting the solution to heating, cooling the solution to precipitation, crystallization, solvent precipitation, spray drying, freeze drying, agitated thin film evaporator (ATFE), evaporation on rotary evaporator under vacuum and the like. Preferably the reaction solution may be cooled to precipitation followed by stirring the reaction mixture for sufficient period of time. Optionally, an anti-solvent may be added to improve the product precipitation prior to cooling the reaction mass. The co-crystals of dapagliflozin can be recovered by any conventional technique known in the art, for example, filtration. The resultant co-crystals of dapagliflozin may optionally be further purified.

In another embodiment, the present invention provides co-crystals of dapagliflozin having a chemical purity greater than or equal to about 97%, as measured by HPLC, preferably about 98% as measured by HPLC, and more preferably about 99.5%, as measured by HPLC.

In another embodiment, some of the co-crystals of the present invention may exist as polymorphs and as such are intended to be included in the present invention. In addition, some of the co-crystals of the present invention may form solvates with water (i.e., hydrates) or common organic solvents, and such solvates are also intended to be encompassed within the scope of this invention.

In another embodiment, the co-crystals of dapagliflozin recovered using the process of the present invention described above includes one or more co-crystals of dapagliflozin such as dapagliflozin DL-pipecolic acid co-crystals, dapagliflozin D-pipecolic acid co-crystals and dapagliflozin L-pipecolic acid co-crystals.

In another embodiment, the present invention provides co-crystals of dapagliflozin, wherein the co-crystal is selected from DL-pipecolic acid, D-pipecolic acid or L-pipecolic acid.

In another embodiment, the present invention provides dapagliflozin DL-pipecolic acid co-crystals.

In another embodiment, the present invention provides a process for the preparation of dapagliflozin DL-pipecolic acid co-crystals, comprising:
  a) providing a solution or suspension comprising dapagliflozin and DL-pipecolic acid in one or more solvents; and
  b) isolating the dapagliflozin DL-pipecolic acid co-crystals.

The step of providing a solution or suspension comprising dapagliflozin and DL-pipecolic acid in one or more solvent may include heating to dissolve. The temperature suitable for dissolving or suspending the dapagliflozin in the one or more solvents depends on the solvent used and the amount of dapagliflozin in the reaction mass. Typically, the solution or suspension is heated at a temperature of at least about 30° C. to about reflux. Examples of one or more c solvents used in step a) are same as solvents defined just as above.

The step b) of the foregoing process, isolation of the dapagliflozin DL-pipecolic acid co-crystals obtained may be carried out by optionally allowing the reaction mass to gradually cool to a temperature of less than 30° C. and the resultant dapagliflozin DL-pipecolic acid co-crystals can be isolated by conventional techniques, for example by filtration. The resultant wet product may optionally be further dried. Drying can be suitably carried out in a tray dryer, vacuum oven, air oven, fluidized bed drier, spin flash dryer, flash dryer and the like.

In another embodiment, dapagliflozin DL-pipecolic acid co-crystals recovered using the process as described just above is substantially a crystalline form.

Figure 9:
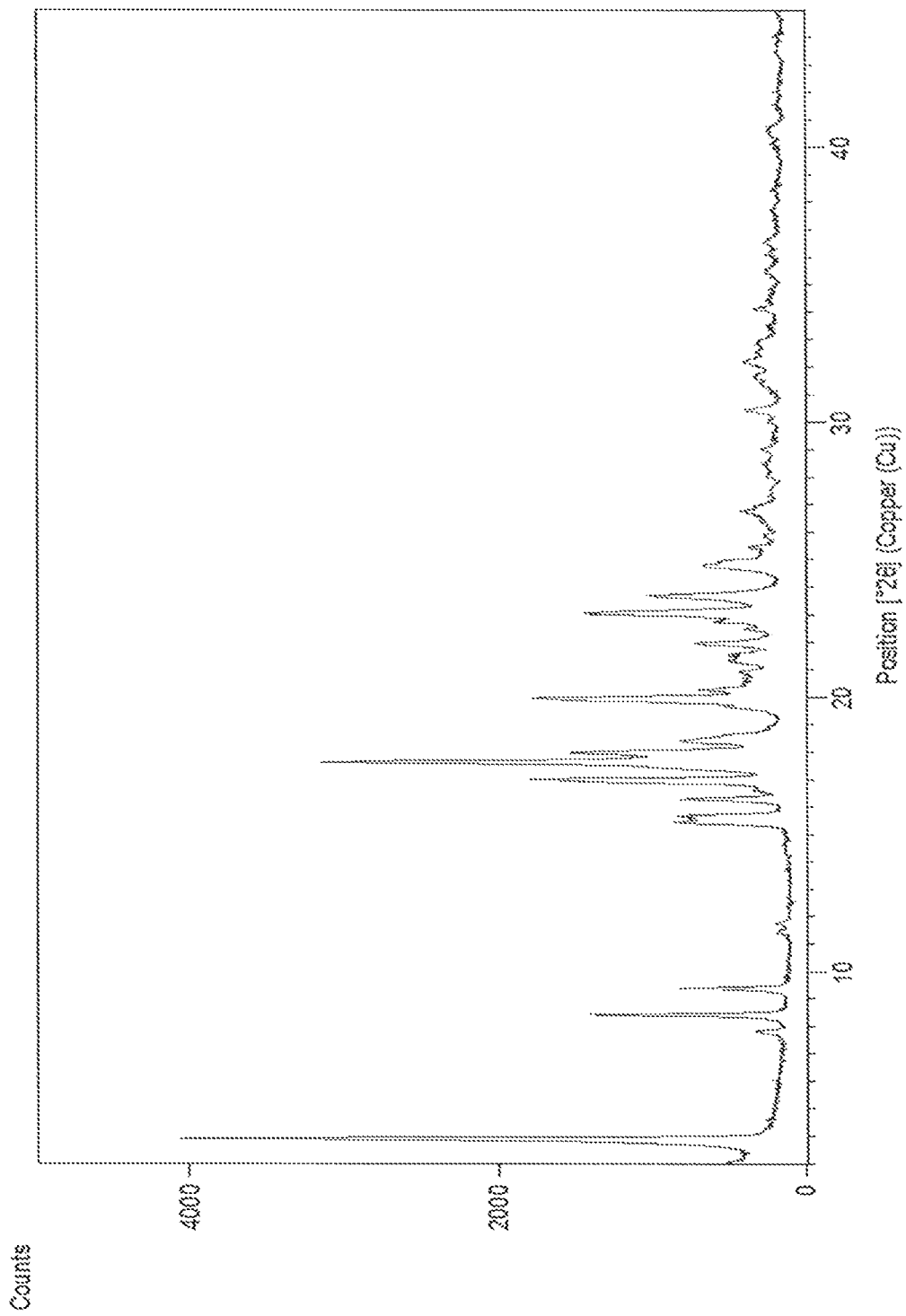
FIG. 9 is the characteristic powder XRD pattern of dapagliflozin DL-pipecolic acid co-crystal.

In another embodiment, the present invention provides dapagliflozin DL-pipecolic acid co-crystals characterized by X-Ray powder diffraction (XRD) pattern substantially in accordance with FIG. 09.

In another embodiment, the present invention provides dapagliflozin DL-pipecolic acid co-crystals characterized by an X-Ray powder diffraction (XRD) pattern having one or more peaks at about 3.91, 7.83, 8.41, 9.38, 11.76, 15.38, 15.65, 16.26, 16.99, 17.62, 17.95, 18.36, 19.96, 20.28, 21.29, 21.97, 23.02, 23.65, 24.68, 26.72, 30.43 and 31.34±0.2° 2θ.

Figure 10:
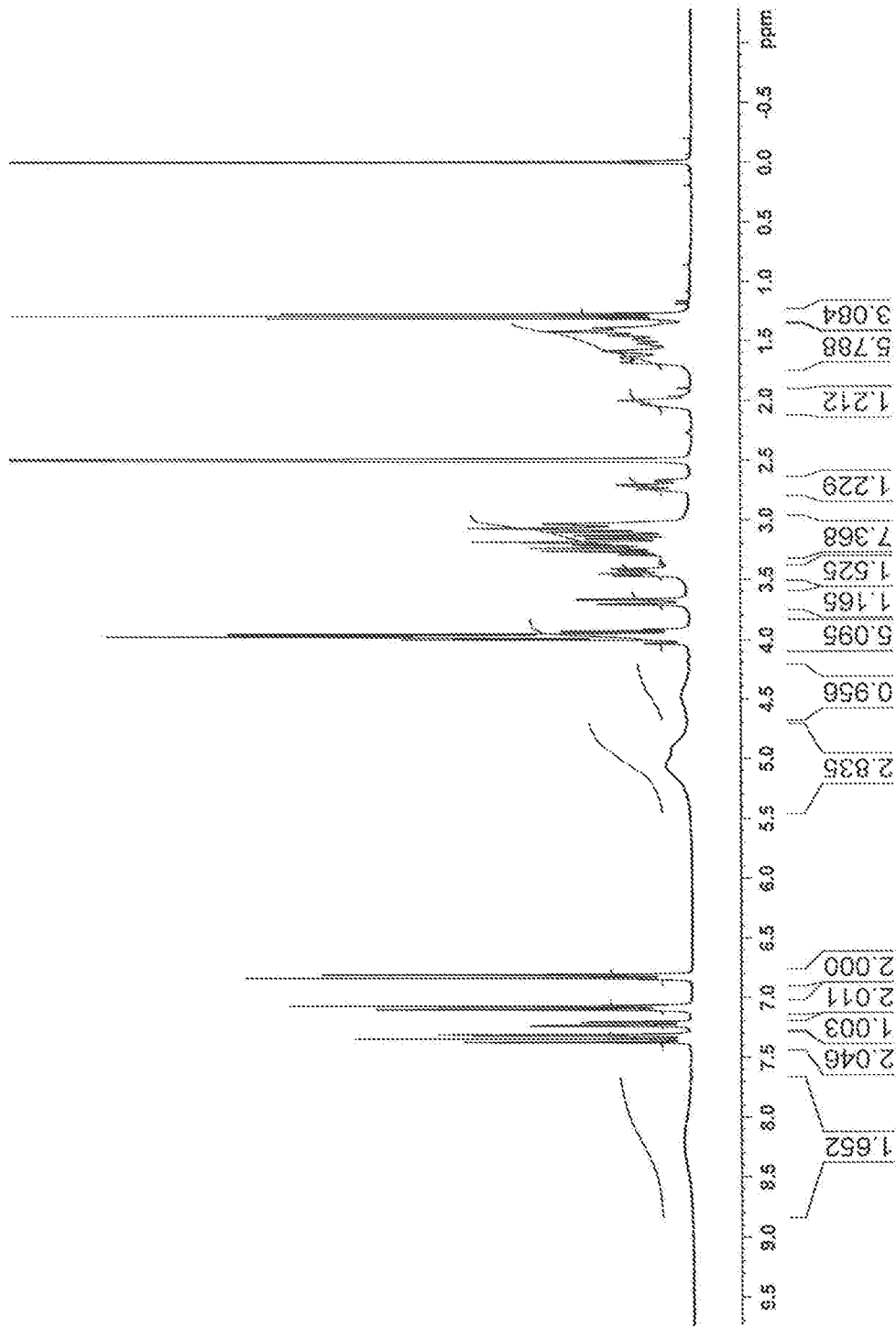
FIG. 10 is the characteristic $^1$H NMR Spectrum of dapagliflozin DL-pipecolic acid co-crystals.

In another embodiment, the present invention provides dapagliflozin DL-pipecolic acid co-crystals characterized by a $^1$H NMR Spectrum substantially in accordance with FIG. 10.

Figure 11:
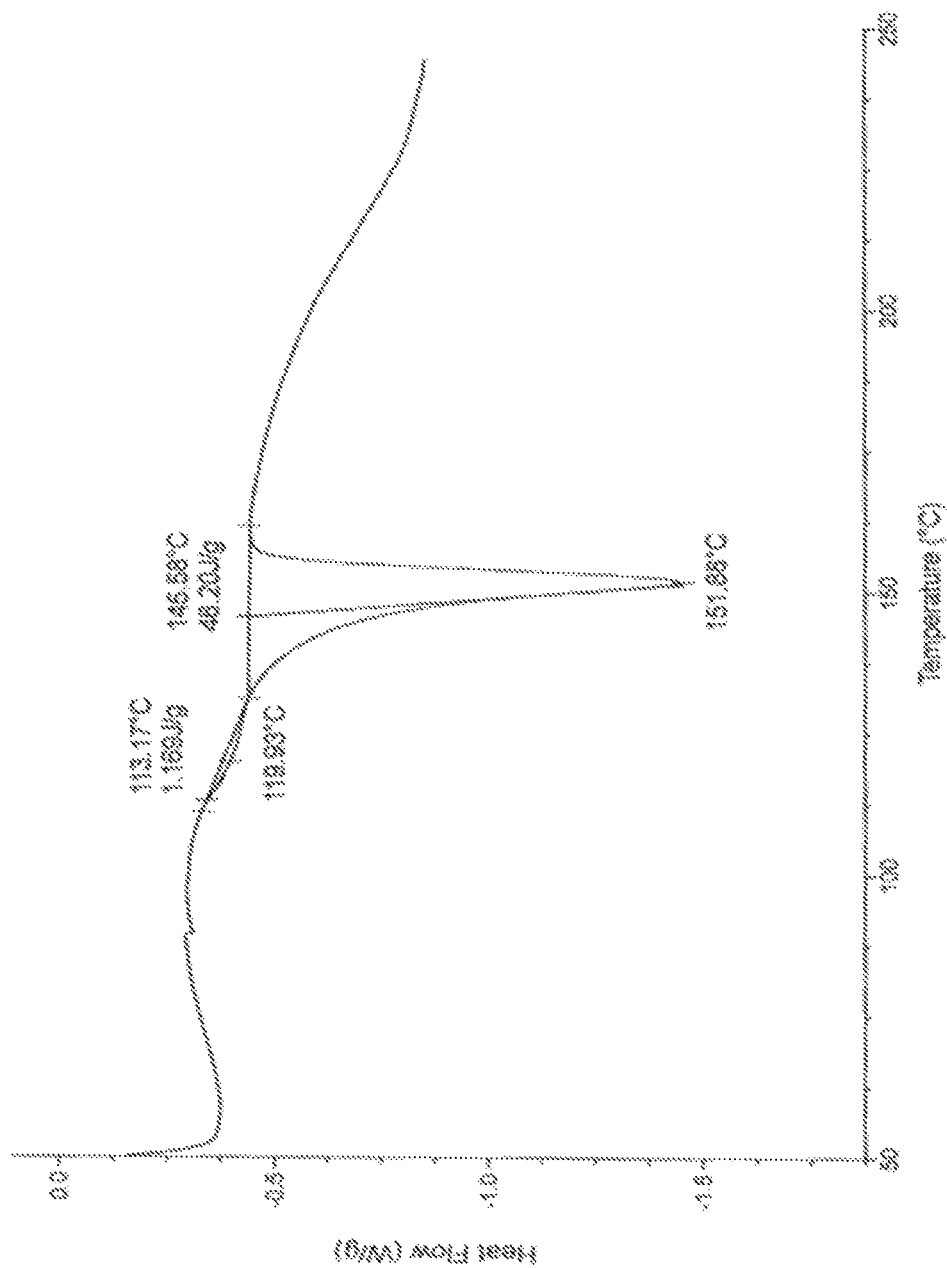
FIG. 11 is the characteristic DSC thermogram of dapagliflozin DL-pipecolic acid co-crystals.

In another embodiment, the present invention provides dapagliflozin DL-pipecolic acid co-crystals characterized by a differential scanning calorimetry (DSC) thermogram substantially in accordance with FIG. 11.

Figure 12:
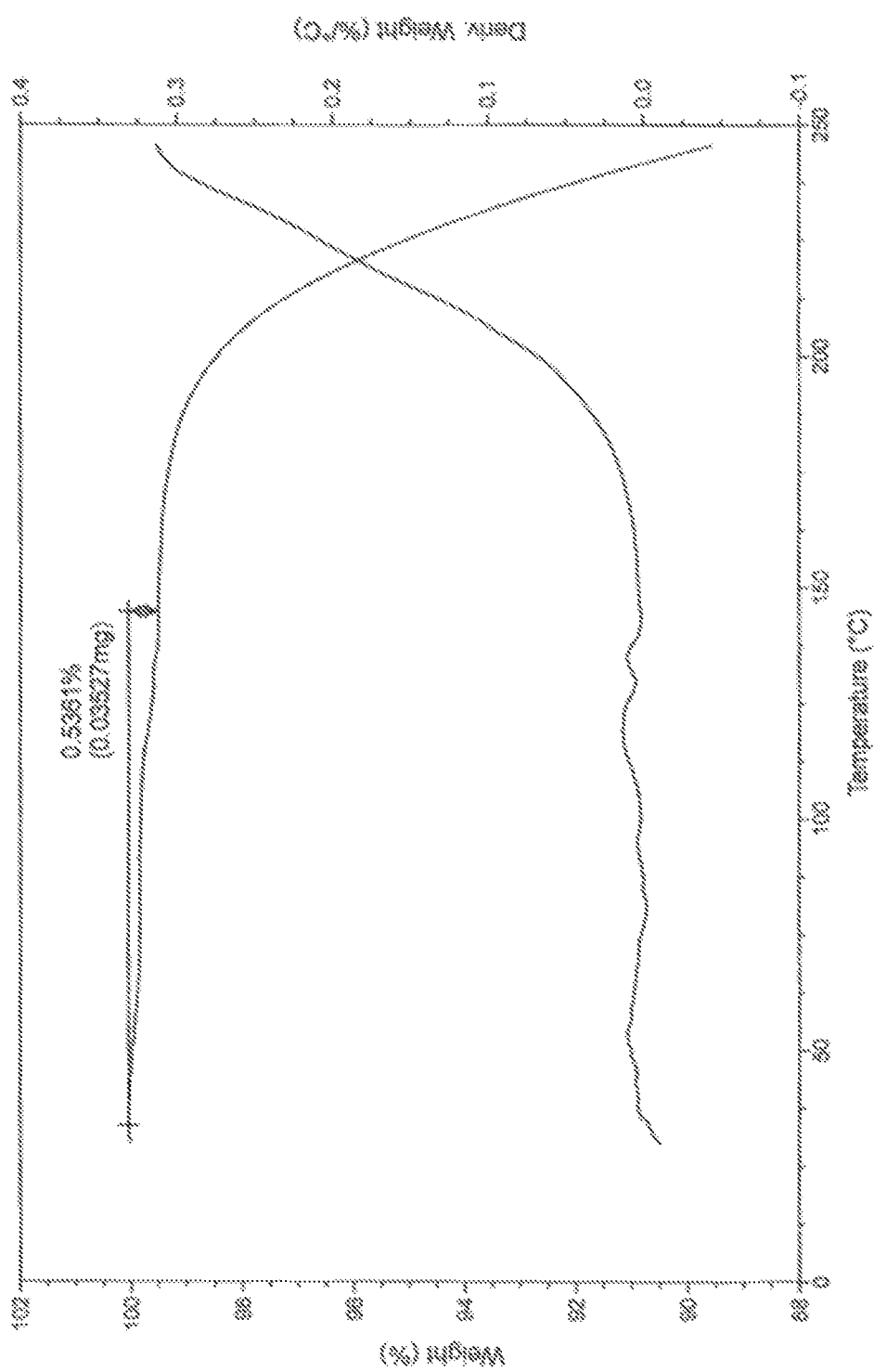
FIG. 12 is the characteristic TGA curve of dapagliflozin DL-pipecolic acid co-crystal.

In another embodiment, the present invention provides dapagliflozin DL-pipecolic acid co-crystals characterized by a thermogravimetric analysis (TGA) curve substantially in accordance with FIG. 12.

In another embodiment, the present invention provides dapagliflozin DL-pipecolic acid co-crystals characterized by X-Ray powder diffraction (XRD) pattern substantially in accordance with FIG. 09, a $^1$H NMR Spectrum substantially in accordance with FIG. 10, a differential scanning calorimetry (DSC) thermogram substantially in accordance with FIG. 11 and a thermogravimetric analysis (TGA) curve substantially in accordance with FIG. 12.

In another embodiment, the present invention provides dapagliflozin D-pipecolic acid co-crystals.

In another embodiment, the present invention provides a process for the preparation of dapagliflozin D-pipecolic acid co-crystals, comprising:
a) providing a solution or suspension comprising dapagliflozin and D-pipecolic acid in one or more solvents; and
b) isolating the dapagliflozin D-pipecolic acid co-crystals.

The step of providing a solution or suspension comprising dapagliflozin and D-pipecolic acid in one or more solvent may include heating to dissolve. The temperature suitable for dissolving or suspending the dapagliflozin in the one or more solvents depends on the solvent used and the amount of dapagliflozin in the reaction mass. Typically, the solution or suspension is heated at a temperature of at least about 30° C. to about reflux. Examples of one or more organic solvents used in step a) are same as solvents defined just as above.

The step b) of the foregoing process, isolation of the dapagliflozin D-pipecolic acid co-crystals obtained may be carried out by optionally allowing the reaction mass to gradually cool to a temperature of less than 30° C. and the resultant dapagliflozin D-pipecolic acid co-crystals can be isolated by conventional techniques, for example by filtration. The resultant wet product may optionally be further dried. Drying can be suitably carried out in a tray dryer, vacuum oven, air oven, fluidized bed drier, spin flash dryer, flash dryer and the like.

In another embodiment, dapagliflozin D-pipecolic acid co-crystals recovered using the process as described just above is substantially a crystalline form.

Figure 13:
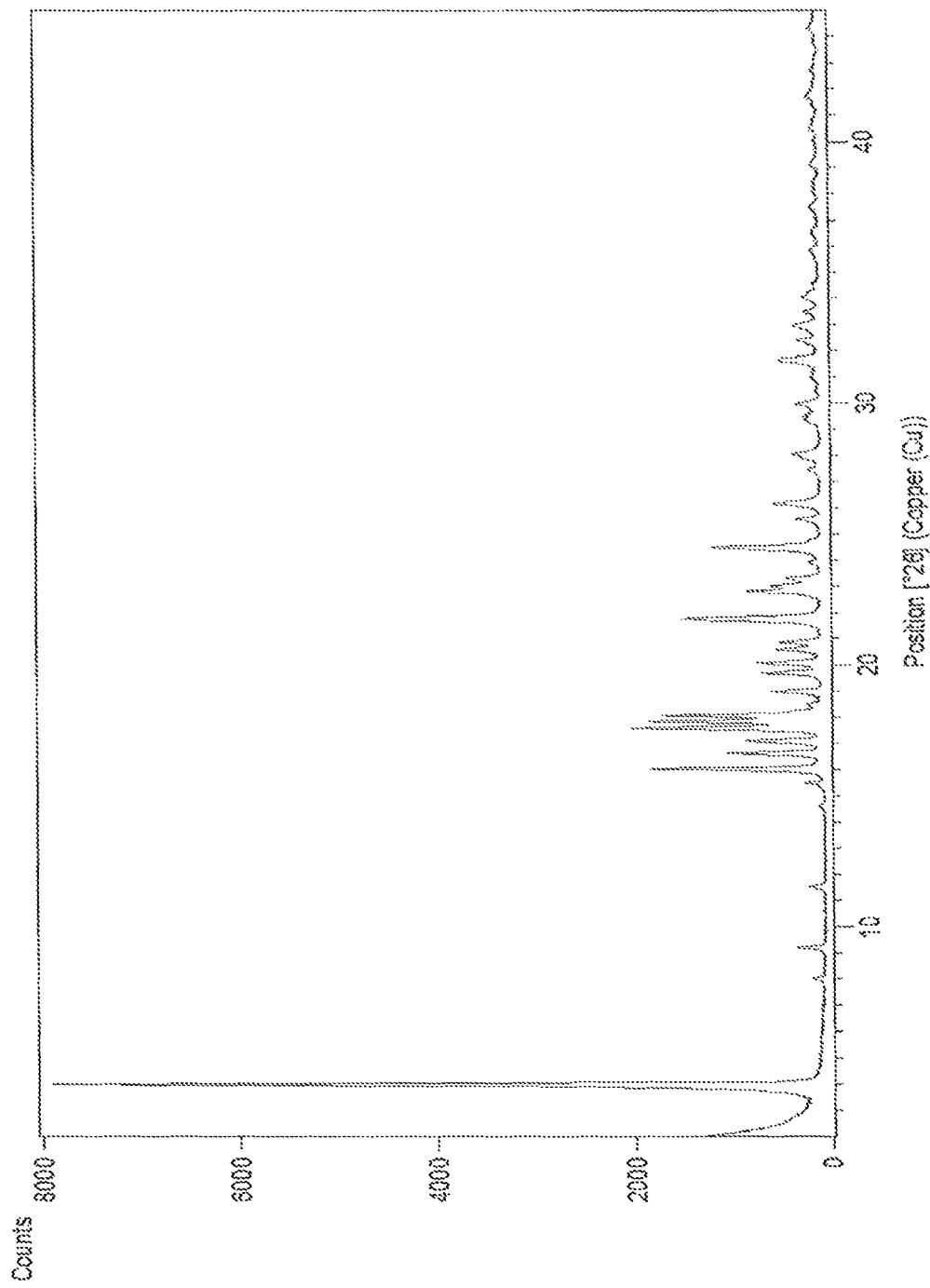
FIG. 13 is the characteristic powder XRD pattern of dapagliflozin D-pipecolic acid co-crystals.

In another embodiment, the present invention provides dapagliflozin D-pipecolic acid co-crystals characterized by X-Ray powder diffraction (XRD) pattern substantially in accordance with FIG. 13.

In another embodiment, the present invention provides dapagliflozin L-pipecolic acid co-crystals.

In another embodiment, the present invention provides a process for the preparation of dapagliflozin L-pipecolic acid co-crystals, comprising:
a) providing a solution or suspension comprising dapagliflozin and L-pipecolic acid in one or more solvents; and
b) isolating the dapagliflozin L-pipecolic acid co-crystals.

The step of providing a solution or suspension comprising dapagliflozin and L-pipecolic acid in one or more solvent may include heating to dissolve. The temperature suitable for dissolving or suspending the dapagliflozin in the one or more solvents depends on the solvent used and the amount of dapagliflozin in the reaction mass. Typically, the solution or suspension is heated at a temperature of at least about 30° C. to about reflux. Examples of one or more organic solvents used in step a) are same as organic solvents defined just as above.

The step b) of the foregoing process, isolation of the dapagliflozin L-pipecolic acid co-crystals obtained may be carried out by optionally allowing the reaction mass to gradually cool to a temperature of less than 30° C. and the resultant dapagliflozin L-pipecolic acid co-crystals can be isolated by conventional techniques, for example by filtration. The resultant wet product may optionally be further dried. Drying can be suitably carried out in a tray dryer, vacuum oven, air oven, fluidized bed drier, spin flash dryer, flash dryer and the like.

In another embodiment, dapagliflozin L-pipecolic acid co-crystals recovered using the process as described just above is substantially a crystalline form.

Figure 14:
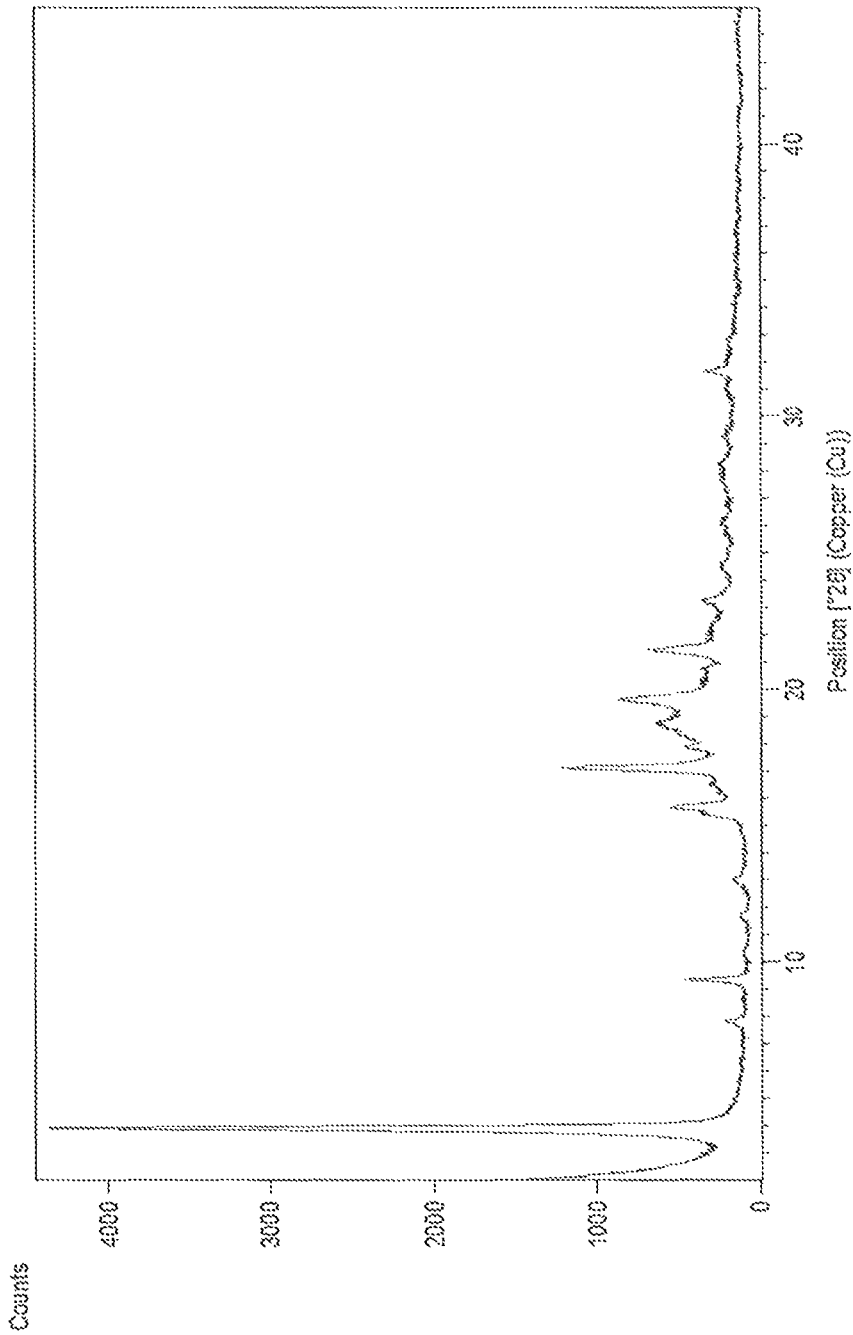
FIG. 14 is the characteristic powder XRD pattern of dapagliflozin L-pipecolic acid co-crystals.

In another embodiment, the present invention provides dapagliflozin L-pipecolic acid co-crystals characterized by X-Ray powder diffraction (XRD) pattern substantially in accordance with FIG. 14.

In another embodiment, the present invention provides solvates of dapagliflozin.

In another embodiment, the present invention provides dapagliflozin 2,3-butanediol solvate.

In another embodiment, the present invention provides crystalline dapagliflozin 2,3-butanediol solvate.

Figure 15:
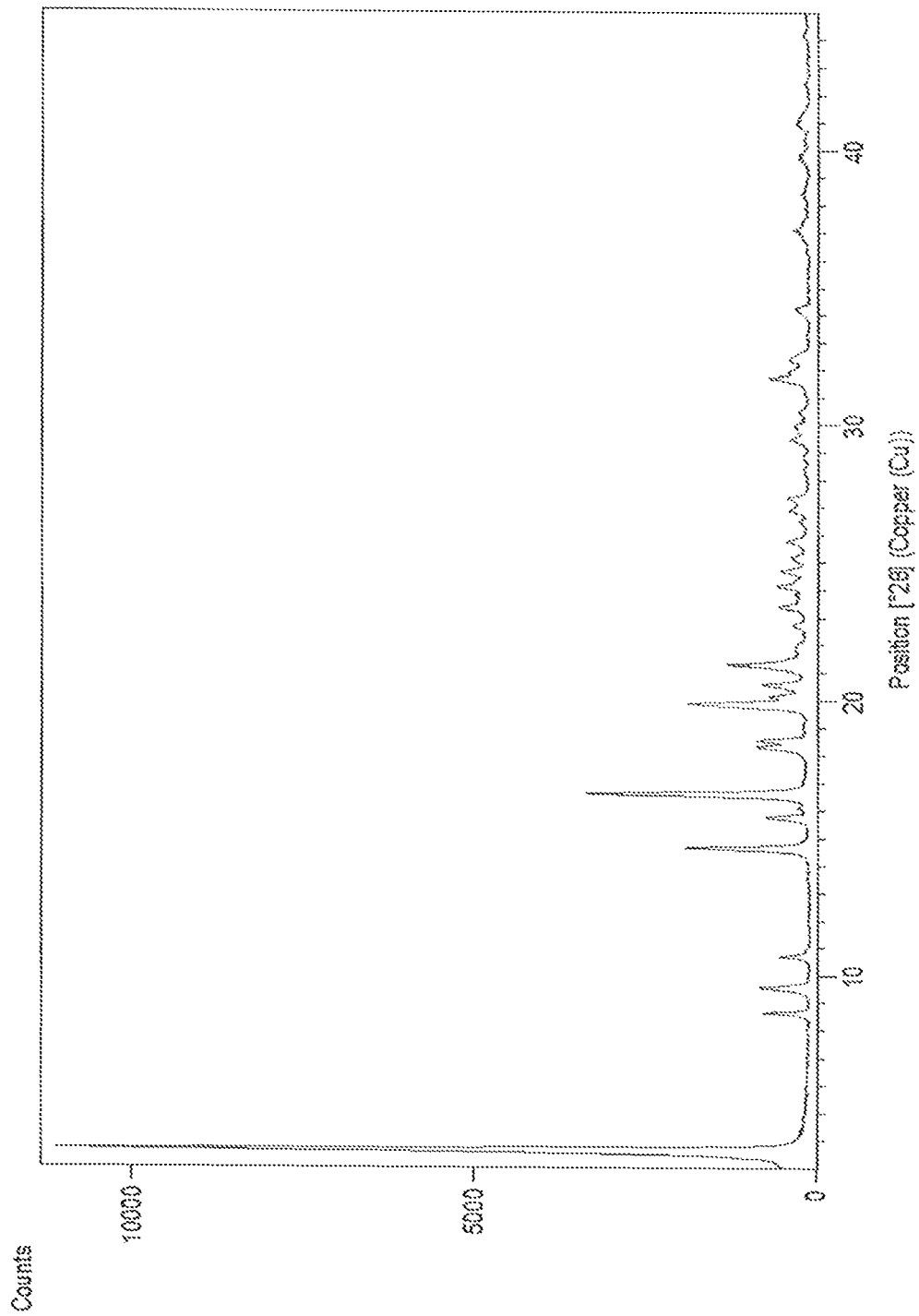
FIG. 15 is the characteristic powder XRD pattern of dapagliflozin 2,3-butanediol solvate.

In another embodiment, crystalline dapagliflozin 2,3-butanediol solvate characterized by X-Ray powder diffraction (XRD) pattern substantially in accordance with FIG. 15.

In another embodiment, the present invention provides crystalline dapagliflozin 2,3-butanediol solvate characterized by X-Ray powder diffraction (XRD) pattern having one or more peaks at about 3.69, 8.62, 9.52, 10.70, 14.63, 15.74, 16.09, 16.60, 18.33, 18.55, 19.82, 20.15, 20.56, 21.20, 21.79, 22.75, 23.39, 24.23, 24.68, 25.15, 25.76, 26.50, 27.03, 27.36, 29.48, 29.94, 30.60, 31.66, 32.56, 34.21 and 36.95±0.2° 2θ.

Figure 16:
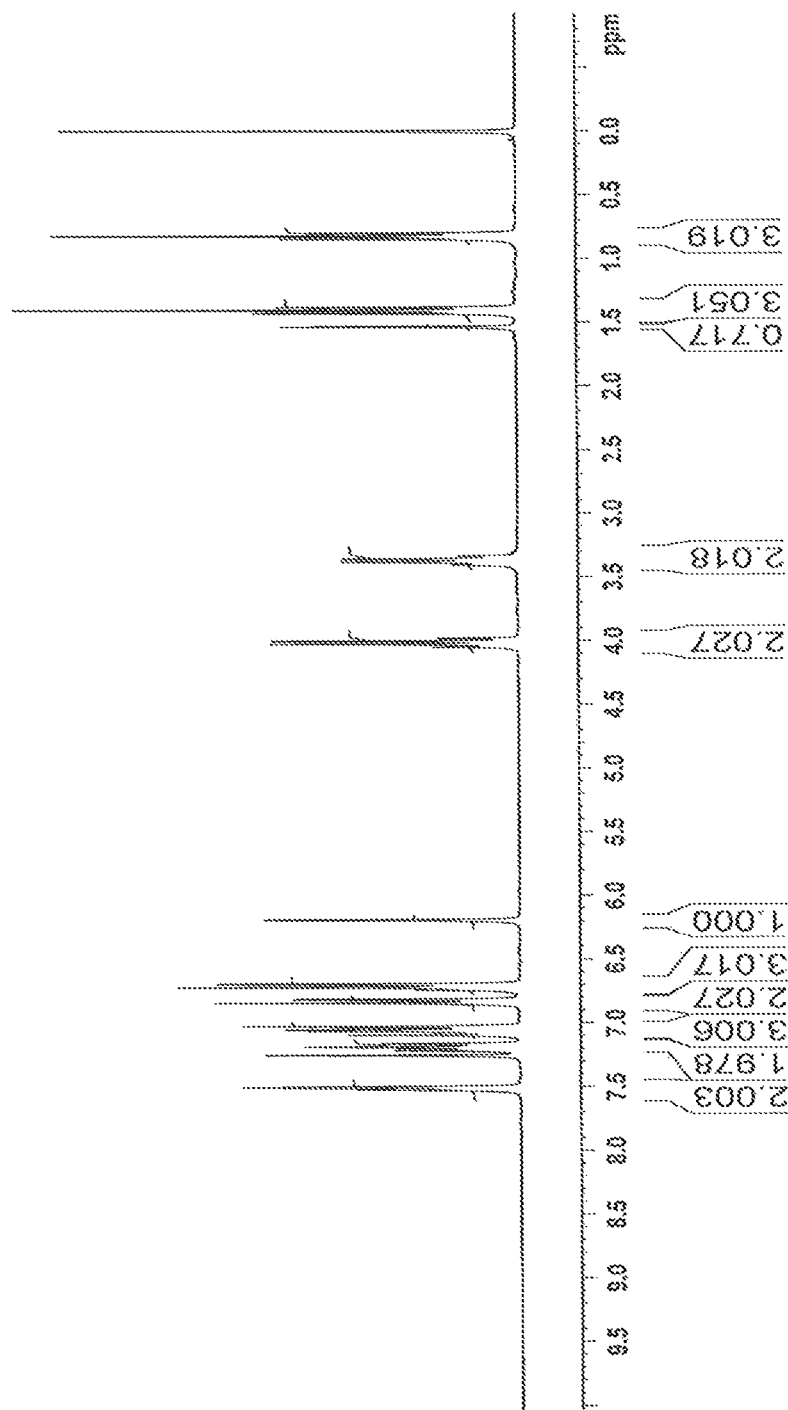
FIG. 16 is the characteristic $^1$H NMR Spectrum of dapagliflozin 2,3-butanediol solvate.

In another embodiment, the present invention provides crystalline dapagliflozin 2,3-butanediol solvate characterized by a $^1$H NMR Spectrum substantially in accordance with FIG. 16.

Figure 17:
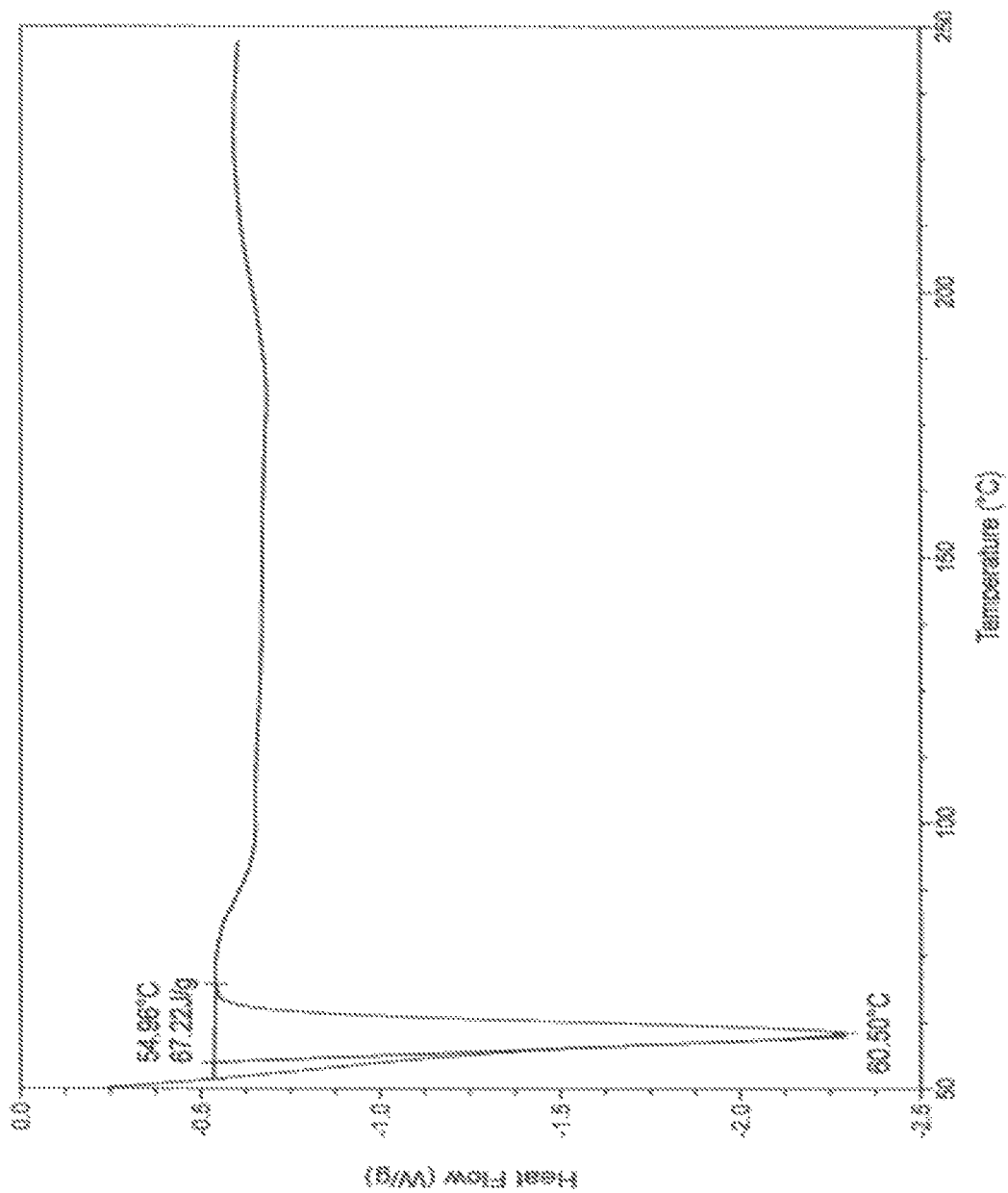
FIG. 17 is the characteristic DSC thermogram of dapagliflozin 2,3-butanediol solvate.

In another embodiment, the present invention provides crystalline dapagliflozin 2,3-butanediol solvate characterized by a differential scanning calorimetry (DSC) thermogram substantially in accordance with FIG. 17.

Figure 18:
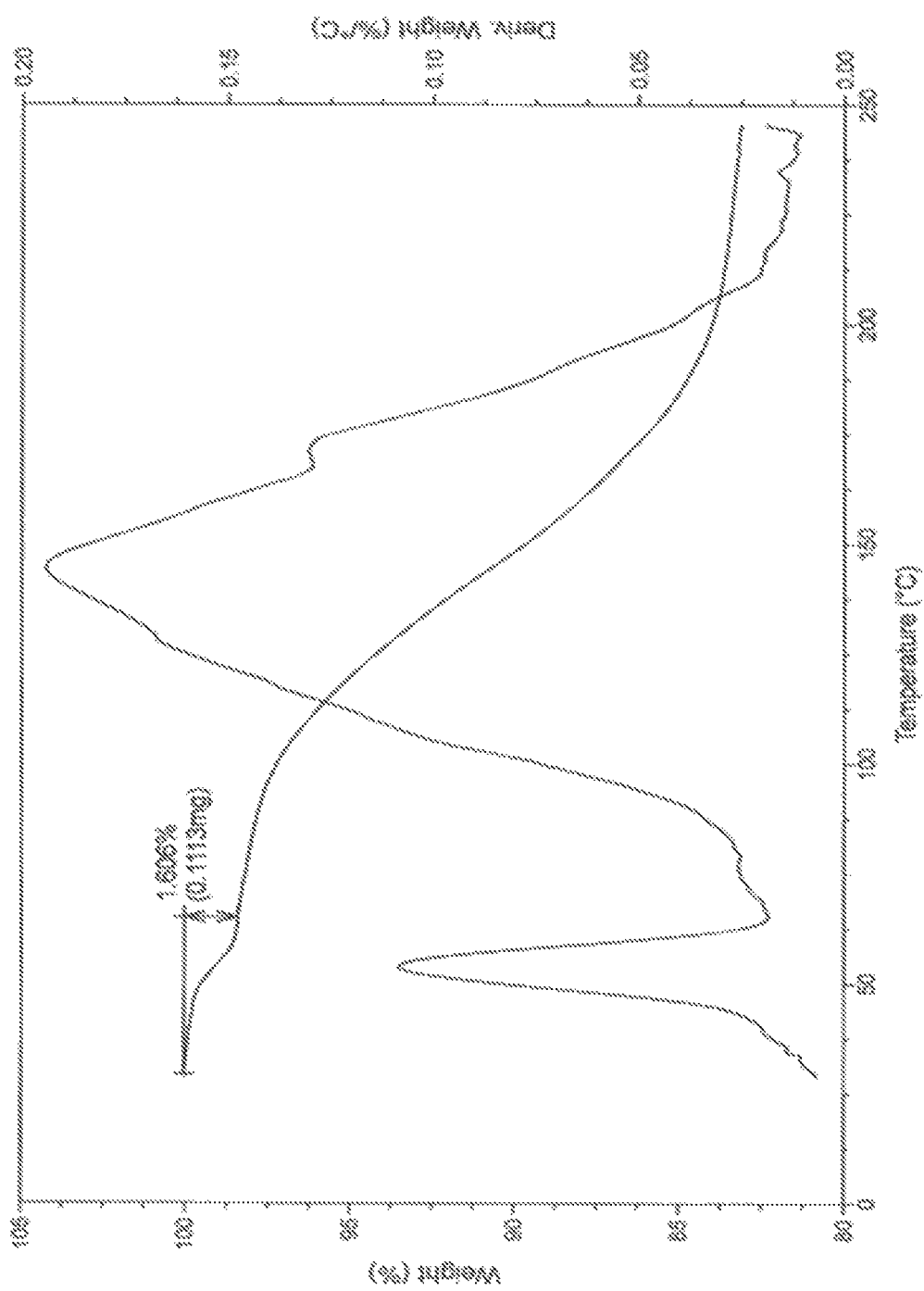
FIG. 18 is the characteristic TGA curve of dapagliflozin 2,3-butanediol solvate.

In another embodiment, the present invention provides crystalline dapagliflozin 2,3-butanediol solvate characterized by a thermogravimetric analysis (TGA) curve substantially in accordance with FIG. 18.

In another embodiment, the present invention provides a process for the preparation of dapagliflozin 2,3-butanediol solvate, comprising:
 a) dissolving dapagliflozin or a solvate or a co-crystal in an organic solvent at a temperature of about 25° C. to reflux,
 b) treating the above solution with 2,3-butanediol,
 c) optionally adding seed crystals of dapagliflozin 2,3-butanediol solvate,
 d) adding an anti-solvent to the reaction mass, and
 e) isolating dapagliflozin 2,3-butanediol solvate.

Step a) of the forgoing process involves the dissolution of dapagliflozin in an organic solvent, wherein the organic solvent includes but are not limited to ethers such as methyl tertiary butyl ether, tetrahydrofuran, dimethyl ether, diisopropyl ether, 1,4-dioxane and the like; esters such as methyl acetate, ethyl acetate, isopropyl acetate, n-propyl acetate, n-butyl acetate, t-butyl acetate and the like; alcohols such as methanol, ethanol, isopropanol, n-propanol, n-butanol, isobutanol and the like; ketones such as acetone, methyl ethyl ketone, methyl isobutyl ketone and the like; nitriles such as acetonitrile, propionitrile or mixtures thereof. Preferably the organic solvent includes methyl tertiary butyl ether, ethyl acetate, isopropyl acetate and mixtures thereof. Optionally the reaction mixture may be heated to complete dissolution of the contents in the solvent. The suitable temperature may be selected from room temperature to about reflux temperature of the solvent used, preferably at about 20° C. to about 75° C. Then the step a) solution of dapagliflozin is treated with 2,3-butanediol and the obtained solution is further stirred.

Adding the solution obtained in step b) to the anti-solvent, or adding an anti-solvent to the solution obtained in step b) to effect the crystallization of the product.

The anti-solvent used for step d) includes but are not limited to water, hydrocarbon solvents such as n-pentane, n-hexane, n-heptane, cyclohexane, methyl cyclohexane, cycloheptane or mixture thereof; preferably heptane, cyclohexane or cycloheptane.

Optionally seed crystals of dapagliflozin 2,3-butanediol solvate may be added either prior to addition of anti-solvent to the reaction solution or during the addition of anti-solvent. The seed crystals can be prepared according the process of the present invention.

In step e) of the foregoing process, the isolation of crystalline dapagliflozin 2,3-butanediol solvate may be carried out by crystallization, solvent precipitation, concentration by subjecting the solution to heating, spray drying, freeze drying, evaporation on rotary evaporator under vacuum, agitated thin film evaporator (ATFE) and the like. Preferably the reaction solution may be cooled to precipitation followed by stirring the reaction mixture for sufficient period of time and the resultant dapagliflozin 2,3-butanediol solvate can be recovered by conventional techniques, for example filtration. The product thus isolated may be optionally dried.

In another embodiment, the present invention provides a process for the preparation of amorphous form of dapagliflozin, wherein the process involves one or more solid forms of dapagliflozin of the invention as intermediates.

In another embodiment, the co-crystals of dapagliflozin of the present invention may be used as an intermediate in the process of obtaining high purity dapagliflozin.

In another embodiment, the present invention provides the use of one or more co-crystals of dapagliflozin, preferably DL-pipecolic acid co-crystals, D-pipecolic acid co-crystals or L-pipecolic acid co-crystals in the preparation of high purity amorphous dapagliflozin.

In another embodiment, the dapagliflozin 2,3-butanediol solvate of the present invention may be used as an intermediate in the process of obtaining high purity dapagliflozin.

In another embodiment, the present invention provides a process for the preparation of amorphous dapagliflozin, comprising:
 a) dissolving or suspending dapagliflozin co-crystals in a suitable solvent;
 b) optionally treating the step a) reaction mass with a suitable base or an acid;
 c) extracting dapagliflozin into an organic solvent; and
 d) removing the solvent to obtain amorphous form of dapagliflozin.

The dapagliflozin co-crystals used in step a) includes but are not limited to amino acid co-crystals such as proline, alanine, valine, leucine, isoleucine, phenyl alanine, tryptophan, glycine, serine, threonine, cysteine, tyrosine, asparagine, glutamine, lysine, arginine, histidine, aspartic acid, glutamic acid, pipecolic acid, wherein the amino acid used may be either optically active or racemic form; ammonia, nicotinic acid, isonicotinic acid, pyridine, pyrazole, pyrazine-2-carboxylic acid, imidazole, morpholine, lactose and citric acid.

Preferably the dapagliflozin co-crystals used herein are selected from dapagliflozin DL-pipecolic acid, D-pipecolic acid or L-pipecolic acids, which are prepared by the processes as described above.

The solvent used herein for dissolution of dapagliflozin co-crystals is selected from water or mixture of water and an organic solvent; wherein organic solvent is selected from alcohols such as methanol, ethanol, 1-propanol, isopropanol, butanol, isobutanol, t-butanol or mixtures thereof; esters such as methyl acetate, ethyl acetate, isopropyl acetate and the like; preferably water, or a mixture of water and an organic solvent such as ethyl acetate.

The temperature suitable for dissolving or suspending the dapagliflozin co-crystals in the one or more suitable solvents depends on the solvent used and the amount of dapagliflozin co-crystals in the reaction mass. Typically, the solution or suspension is stirred at a temperature of at least about 20° C. to about reflux.

Step b) of the foregoing process involves treating the step a) reaction mass with a base or an acid before extracting the dapagliflozin into an organic solvent. The base or acid may be added from about 0.5 to about 5 mole equivalents per mole of starting co-crystals of dapagliflozin, preferably about 1 to about 4 moles.

Suitable base is either inorganic or organic base. The inorganic base is selected from the group comprising alkali metal carbonates such as sodium carbonate, potassium carbonate, cesium carbonate; alkali metal bicarbonates such as sodium bicarbonate, potassium bicarbonate and the like; alkali metal hydroxides such as sodium hydroxide, potassium hydroxide and lithium hydroxide and the like. The organic base used herein is selected from the group comprising of alkyl amines such as di-isopropyl ethylamine, triethyl amine and the like; heterocyclic amines such as pyridine and the like. The suitable base can be added either as a solution in one or more solvents as herein before defined or it may be added directly to the solution of co-crystals of dapagliflozin in one or more solvents.

Suitable acid is selected from the group comprising of hydrochloric acid, sulfuric acid, acetic acid or mixtures thereof.

Examples of organic solvents used for extraction herein includes but are not limited to esters such as methyl acetate, ethyl acetate, isopropyl acetate n-propyl acetate, n-butyl acetate, t-butyl acetate and the like; ethers such as dimethyl ether, diisopropyl ether, methyl tertiary butyl ether, 1,4-dioxane and the like; aliphatic hydrocarbons such as hexane, heptane, pentane and the like; aromatic hydrocarbons such as toluene, xylene and the like; halogenated hydrocarbons such as dichloromethane, chloroform and the like or mixtures thereof.

Isolation of dapagliflozin can be carried out by separating the product containing organic layer and removal of solvent. Techniques which may be used for the removal of solvent include distillation, distillation under vacuum, spray drying, agitated thin film drying ("ATFD") and freeze drying (lyophilization). Preferably isolation of dapagliflozin can be carried out by removal of solvent by distillation under vacuum.

In another embodiment, the present invention provides a process for the preparation of amorphous dapagliflozin, comprising:
  a) dissolving or suspending dapagliflozin co-crystals in a suitable solvent,
  b) treating the step a) reaction mass with a suitable base or an acid,
  c) optionally extracting dapagliflozin into an organic solvent,
  d) removing the solvent to obtain a residue,
  e) dissolving the residue in an organic solvent to obtain a solution,
  f) adding an anti-solvent to the step e) solution or vice-versa,
  g) optionally seeding with amorphous dapagliflozin, and
  h) isolating amorphous dapagliflozin.

The co-crystals of dapagliflozin of step a) comprises one or more of co-crystals as defined herein above and the suitable solvent of step a) also comprises one or more of solvents as defined herein above.

Step b) of the foregoing process involves the treatment of step a) reaction mass with a suitable base or an acid before extracting the dapagliflozin into an organic solvent, wherein suitable base or an acid of step b) and extraction solvent of step c) are defined herein above.

Step d) of the foregoing process involves the removal of solvent to obtain dapagliflozin residue, wherein removal of solvent includes evaporation, distillation or distillation under vacuum; preferably distillation under vacuum.

The residue obtained is dissolved in an organic solvent, wherein the organic solvent includes but are not limited to ethers such as methyl tertiary butyl ether, tetrahydrofuran, dimethyl ether, diisopropyl ether, 1,4-dioxane and the like; esters such as methyl acetate, ethyl acetate, isopropyl acetate, n-propyl acetate, n-butyl acetate, t-butyl acetate and the like; alcohols such as methanol, ethanol, isopropanol, n-propanol, n-butanol, isobutanol and the like; ketones such as acetone, methyl ethyl ketone, methyl isobutyl ketone and the like or mixtures thereof.

The dissolution temperatures may range from about 20° C. to about reflux temperature of the solvent. Then, the amorphous form can be precipitated by mixing an anti-solvent with the reaction solution. The anti-solvent may be either added to step e) solution or step e) solution is added to anti solvent.

The anti-solvent used herein includes but are not limited to water, hydrocarbon solvents such as n-pentane, n-hexane, 3-methylpentane, 2,3-dimethylbutane, n-heptane, 2,3-dimethylpentane, 2,4-dimethylpentane, 3,3-dimethylpentane, 3-ethylpentane, 2,2,3-trimethylbutane, n-octane, 3-methylheptane, cyclohexane, methylcyclohexane, cycloheptane or mixtures thereof; preferably water, heptane or cycloheptane.

The anti-solvent may be added by a single lot manner or by a multiple lots. Prior to addition of anti-solvent, reaction mass temperature may be cooled to less than 30° C., preferably less than 20°. During each lot of anti-solvent addition, reaction mass may be maintained for a minimum of about 5 minutes for better precipitation of the product.

Optionally, amorphous dapagliflozin seed may be added either prior to addition of anti-solvent to the reaction solution or during the addition of anti-solvent. The amorphous dapagliflozin seed can be prepared according the process of the present invention or can be prepared by any known methods.

The step of isolation of the resultant amorphous form can be carried out by conventional technique known in the art, for example filtration. The resultant wet product may optionally be further dried. Drying can be suitably carried out in a tray dryer, vacuum oven, air oven, fluidized bed drier, spin flash dryer, flash dryer and the like.

In another embodiment, the present invention provides a process for the preparation of amorphous dapagliflozin, comprising:
  a) providing a solution of dapagliflozin in a solvent selected from the group consisting of esters, ethers, alcohols, ketones, nitriles or mixtures thereof, and
  b) removing the solvent from the solution to obtain amorphous form of Dapagliflozin.

Step a) of the forgoing process involves the dissolution of dapagliflozin in a solvent, wherein the solvent includes but are not limited to esters such as methyl acetate, ethyl acetate, isopropyl acetate, n-propyl acetate, n-butyl acetate, t-butyl acetate and the like; ethers such as methyl tertiary butyl ether, tetrahydrofuran, dimethyl ether, diisopropyl ether, 1,4-dioxane and the like; alcohols such as methanol, ethanol, isopropanol, n-propanol, n-butanol, isobutanol and the like; ketones such as acetone, methyl ethyl ketone, methyl isobutyl ketone and the like; nitriles such as acetonitrile, propionitrile or mixtures thereof; preferably methyl acetate, isopropyl acetate, ethyl acetate, methyl tertiary butyl ether or mixtures thereof.

The dissolution temperatures may range from about 30° C. to about reflux temperature of the solvent. The step of removal of solvent may be carried out by one or more techniques of distillation, distillation under vacuum, spray drying, agitated thin film drying ("ATFD"), and freeze drying (lyophilization). The resultant wet product may optionally be further dried. Drying can be suitably carried out in a tray dryer, vacuum oven, air oven, fluidized bed drier, spin flash dryer, flash dryer and the like.

In another embodiment, the present invention provides a process for the preparation of amorphous dapagliflozin, comprising:
  a) providing a solution of dapagliflozin in a solvent selected from the group consisting of esters, ethers, alcohols, ketones, nitriles or mixtures thereof,
  b) adding an anti-solvent to the solution or vice versa,
  c) optionally seeding with amorphous dapagliflozin, and d) isolating amorphous form of dapagliflozin; wherein the anti-solvent is selected from the group consisting of water, hydrocarbons solvents, ether solvents or mixtures thereof.

Step a) of the foregoing process involves providing a solution of dapagliflozin in a solvent or mixture of solvent. The solution for step a) can be obtained by the known methods that include: (i) direct use of a reaction mixture containing dapagliflozin that is obtained in the course of its synthesis; or (ii) dissolving dapagliflozin in one or more of organic solvent.

The organic solvent comprises one or more of solvents selected from esters such as methyl acetate, ethyl acetate, isopropyl acetate, n-propyl acetate, n-butyl acetate, t-butyl acetate and the like; ethers such as methyl tertiary butyl ether, tetrahydrofuran, dimethyl ether, diisopropyl ether, 1,4-dioxane and the like; alcohols such as methanol, ethanol, isopropanol, n-propanol, n-butanol, isobutanol and the like; ketones such as acetone, methyl ethyl ketone, methyl isobutyl ketone and the like; nitriles such as acetonitrile, propionitrile or mixtures thereof;

preferably methyl acetate, isopropyl acetate, ethyl acetate, methyl tertiary butyl ether or mixtures thereof.

The dissolution temperatures may range from about 20° C. to about reflux temperature of the solvent. Then, the amorphous form can be precipitated by mixing an anti-solvent with the reaction solution. The anti-solvent may be either added to step a) solution or step a) solution is added to anti solvent.

The anti-solvent used herein includes but are not limited to water, hydrocarbons solvents such as n-pentane, n-hexane, 3-methylpentane, 2,3-dimethylbutane, n-heptane, 2,3-dimethylpentane, 2,4-dimethylpentane, 3,3-dimethylpentane, 3-ethylpentane, 2,2,3-trimethylbutane, n-octane, 3-methylheptane, cyclohexane, methylcyclohexane, cycloheptane or mixtures thereof; preferably water, heptane or cycloheptane.

The anti-solvent may be added by a single lot manner or by a multiple lots. Prior to addition of anti-solvent, reaction mass temperature may be cooled to less than 30° C., preferably less than 20°. During each lot of anti-solvent addition, reaction mass may be maintained for a minimum of about 5 minutes to better precipitation of the product.

Optionally, amorphous dapagliflozin seed may be added either prior to addition of anti-solvent to the reaction solution or during the addition of anti-solvent. The amorphous dapagliflozin seed can be prepared according the process of the present invention or can be prepared by any known methods.

The step of isolation of the resultant amorphous form can be carried out by conventional technique known in the art, for example filtration. The resultant wet product may optionally be further dried. Drying can be suitably carried out in a tray dryer, vacuum oven, air oven, fluidized bed drier, spin flash dryer, flash dryer and the like.

In another embodiment, the present invention provides co-crystals of empagliflozin.

In accordance with another embodiment, the present invention provides co-crystals of empagliflozin, wherein the co-crystal former is selected from the group comprising DL-pipecolic acid, D-pipecolic acid, L-pipecolic acid, ammonia, nicotinic acid, isonicotinic acid, pyridine, pyrazole, pyrazine-2-carboxylic acid, imidazole, morpholine, proline and the like.

In accordance with another embodiment, the present invention provides a process for the preparation of co-crystals of empagliflozin, comprising:

a) providing a solution or suspension comprising empagliflozin and a co-crystal former, and b) isolating the co-crystals of empagliflozin; wherein the co-crystal former is selected from the group comprising DL-pipecolic acid, D-pipecolic acid, L-pipecolic acid, ammonia, nicotinic acid, isonicotinic acid, pyridine, pyrazole, pyrazine-2-carboxylic acid, imidazole, morpholine, proline and the like.

The step of providing a solution or suspension includes any form of empagliflozin that may be mixed with one or more solvents and co-crystal former or includes any form of empagliflozin that may be combined with one or more solvents and then the co-crystal former may be mixed with the resulting solution or slurry. Alternatively, the mixture may be formed by adding empagliflozin and co-crystal former at the same time in to one or more solvents.

Examples of one or more solvents of step a) includes but are not limited to esters such as methyl acetate, ethyl acetate, isopropyl acetate, n-propyl acetate, n-butyl acetate, t-butyl acetate and the like; alcohols such as methanol, ethanol, isopropanol, n-propanol, n-butanol, isobutanol and the like; ethers such as tetrahydrofuran, dimethyl ether, diisopropyl ether, methyl tertiary butyl ether, 1,4-dioxane and the like; ketones such as acetone, methyl ethyl ketone, methyl isobutyl ketone and the like; aliphatic hydrocarbon solvents such as hexane, heptane, cyclohexane and the like; halogenated hydrocarbon solvents such as dichloromethane, dichloroethane, chloroform and the like; nitriles such as acetonitrile, propionitrile and the like; water or mixtures thereof; preferably the solvent of step a) is n-butanol, ethanol or acetone; more preferably n-butanol.

The temperature suitable for dissolving or suspending the empagliflozin in one or more solvents depends on the solvent used and the amount of empagliflozin in the reaction mass. Typically, the solution or suspension is heated at a temperature of at least about 30° C. to about reflux.

The step b) of the foregoing process, the isolation of co-crystals of empagliflozin may be carried out by concentration by subjecting the solution to heating, cooling the solution to precipitation, crystallization, solvent precipitation, spray drying, freeze drying, agitated thin film evaporator (ATFE), evaporation on rotary evaporator under vacuum and the like. Preferably the reaction solution may be cooled to precipitation followed by stirring the reaction mixture for sufficient period of time. Optionally, an anti-solvent can be added to improve the product precipitation prior to cooling the reaction mass. The anti-solvent used herein for example water. The co-crystals of empagliflozin can be recovered by any conventional technique known in the art, for example, filtration. The resultant co-crystals of empagliflozin may optionally be further purified.

In another embodiment, the present invention provides co-crystals of empagliflozin having a chemical purity greater than or equal to about 97%, as measured by HPLC, preferably about 98% as measured by HPLC, and more preferably about 99.5%, as measured by HPLC.

In another embodiment, some of the co-crystals of the present invention may exist as polymorphs and as such are intended to be included in the present invention. In addition, some of the co-crystals of the present invention may form solvates with water (i.e., hydrates) or common organic solvents, and such solvates are also intended to be encompassed within the scope of this invention.

In another embodiment, the co-crystals of empagliflozin recovered using the process of the present invention described above includes empagliflozin DL-pipecolic acid co-crystals.

In another embodiment, the present invention provides empagliflozin DL-pipecolic acid co-crystal.

In another embodiment, the present invention provides empagliflozin DL-pipecolic acid co-crystal hydrate.

In another embodiment, the present invention provides a process for the preparation of empagliflozin DL-pipecolic acid co-crystals, comprising:
a) providing a solution or suspension comprising empagliflozin and DL-pipecolic acid in one or more solvents; and
b) isolating the empagliflozin DL-pipecolic acid co-crystals.

The step of providing a solution or suspension comprising empagliflozin and DL-pipecolic acid in one or more solvent may include heating to dissolve. The temperature suitable for dissolving or suspending the empagliflozin in the one or more solvents depends on the solvent used and the amount of empagliflozin in the reaction mass. Typically, the solution or suspension is heated at a temperature of at least about 30° C. to about reflux. Examples of one or more solvents used in step a) are same as solvents defined just as above.

The step b) of the foregoing process, isolation of the empagliflozin DL-pipecolic acid co-crystal obtained may be carried out by optionally allowing the reaction mass to gradually cool to a temperature of less than 30° C. and the resultant empagliflozin DL-pipecolic acid co-crystals can be isolated by conventional techniques, for example by filtration. The resultant wet product may optionally be further dried. Drying can be suitably carried out in a tray dryer, vacuum oven, air oven, fluidized bed drier, spin flash dryer, flash dryer and the like.

In another embodiment, empagliflozin DL-pipecolic acid co-crystals are recovered using the process as described just above is a hydrate form.

In another embodiment, empagliflozin DL-pipecolic acid monohydrate co-crystals is recovered using the process as described just above is substantially a crystalline form.

Figure 21:
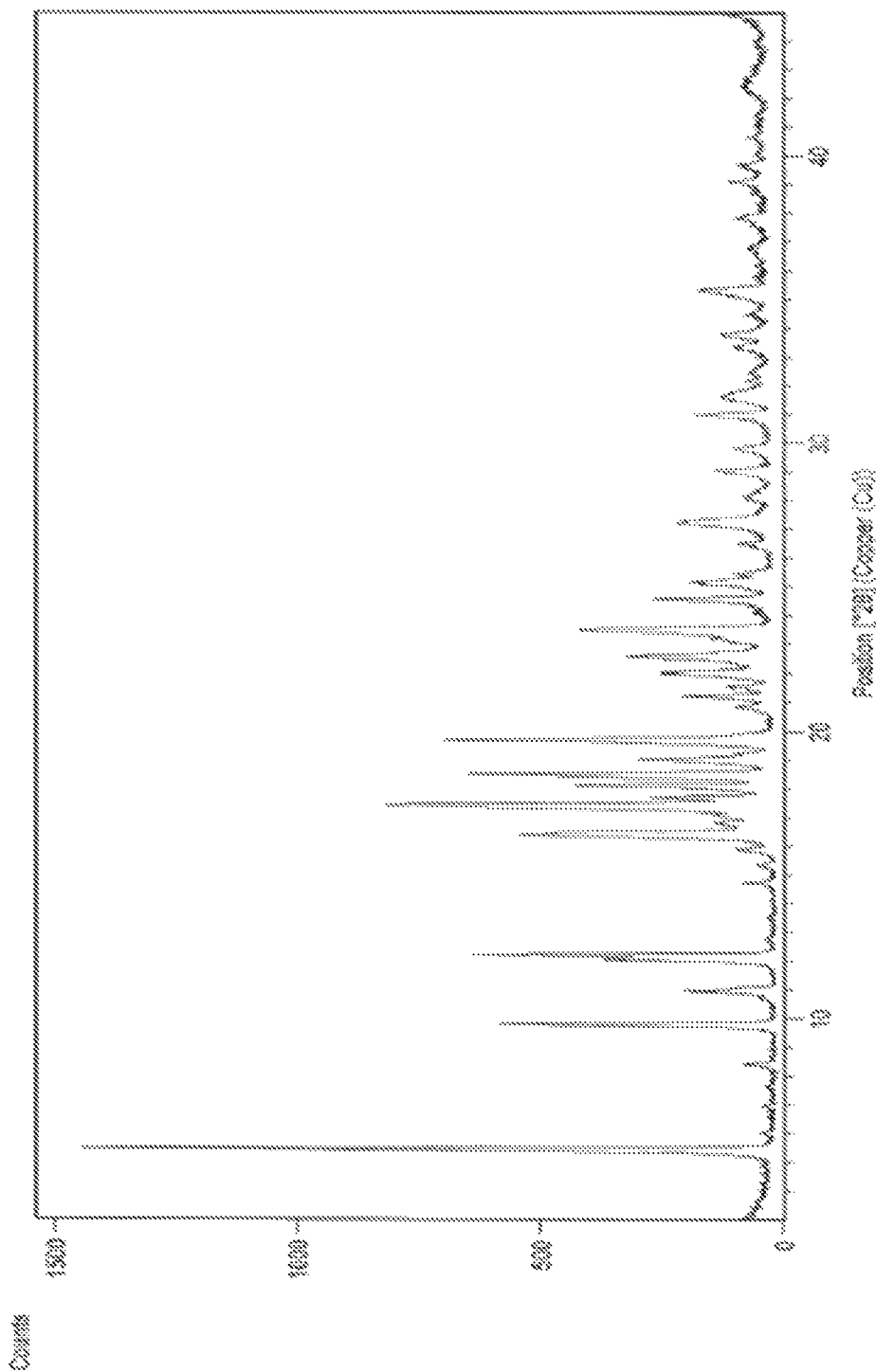
FIG. 21 is the characteristic powder XRD pattern of empagliflozin DL-pipecolic acid co-crystals.

In another embodiment, the present invention provides empagliflozin DL-pipecolic acid co-crystals characterized by X-Ray powder diffraction (XRD) pattern substantially in accordance with FIG. 21.

In another embodiment, the present invention provides empagliflozin DL-pipecolic acid co-crystals characterized by X-Ray powder diffraction (XRD) pattern having one or more peaks at about 5.5, 9.8, 11.0, 12.0, 12.2, 14.7, 15.8, 16.3, 17.3, 17.7, 18.1, 18.5, 18.9, 19.6, 20.7, 21.1, 22, 22.5, 23.5, 24.5, 25.0, 26.4, 27.2, 28.1, 29, 29.8, 30.9, 31.4, 33.7, 35.3, 36.7, 39.6±0.2° 2θ.

Figure 22:
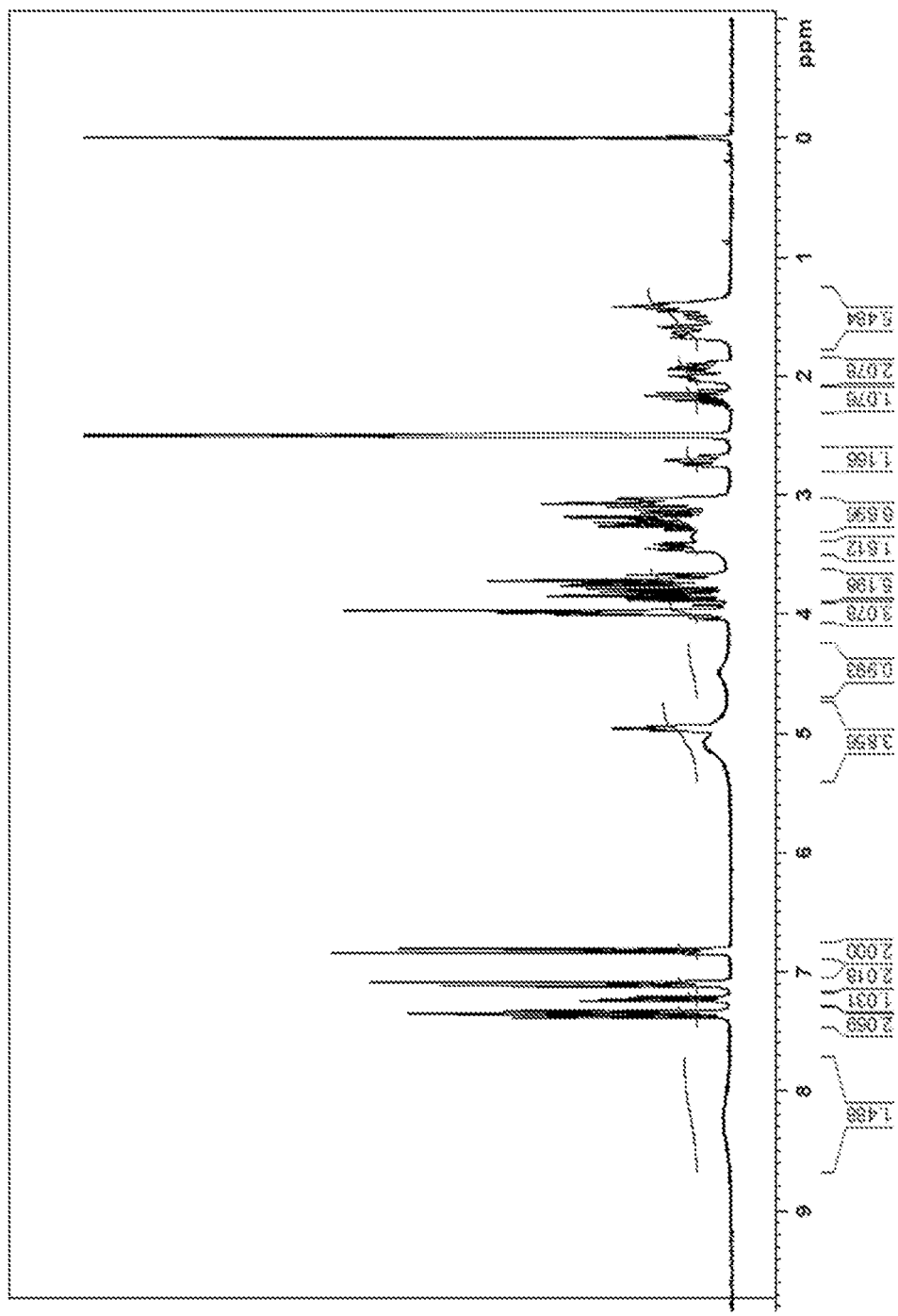
FIG. 22 is the characteristic $^1$H NMR Spectrum of empagliflozin DL-pipecolic acid co-crystals.

In another embodiment, the present invention provides empagliflozin DL-pipecolic acid co-crystals characterized by a $^1$H NMR Spectrum substantially in accordance with FIG. 22.

Figure 23:
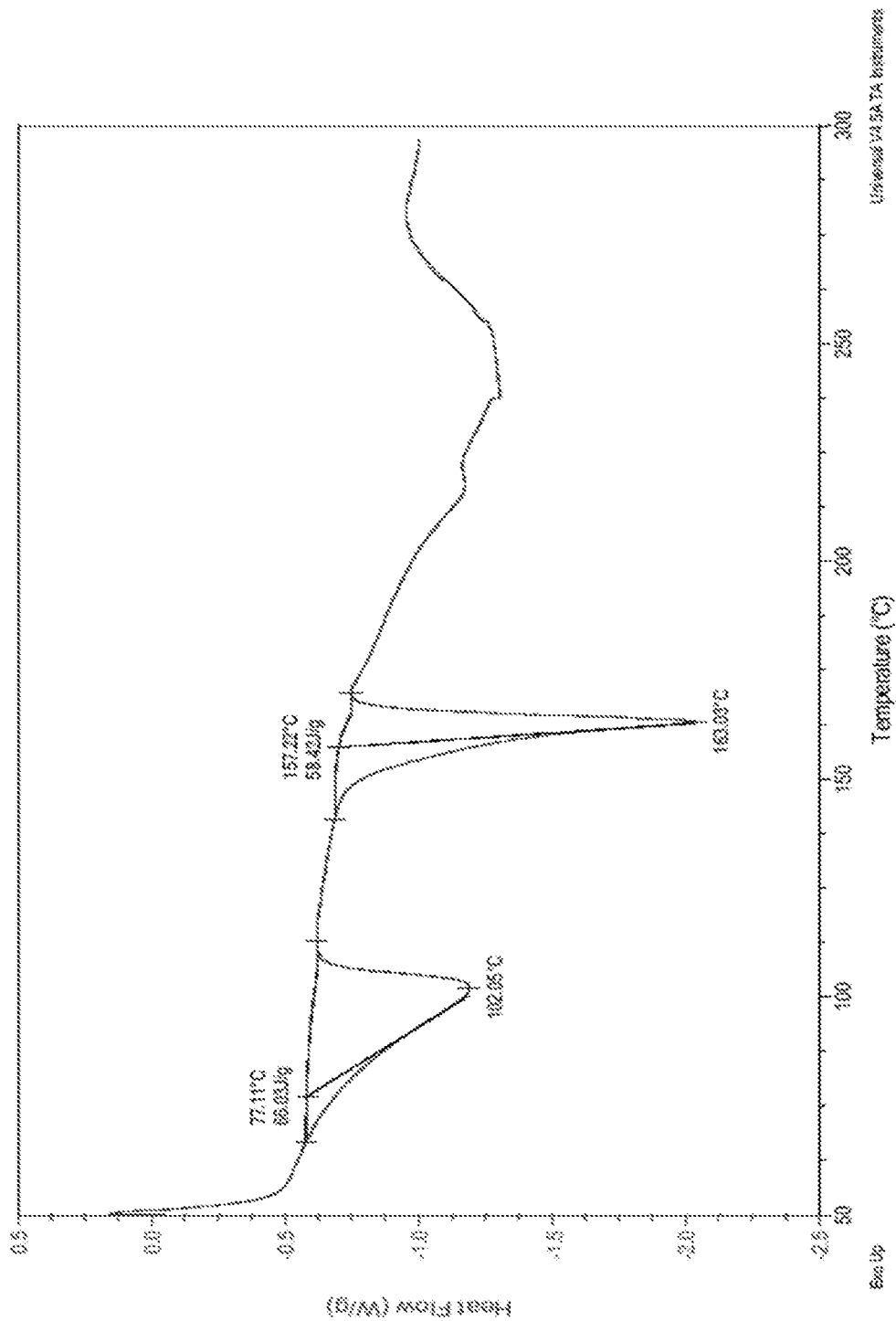
FIG. 23 is the characteristic DSC thermogram of empagliflozin DL-pipecolic acid co-crystals.

In another embodiment, the present invention empagliflozin DL-pipecolic acid co-crystals characterized by a differential scanning calorimetry (DSC) thermogram substantially in accordance with FIG. 23.

Figure 24:
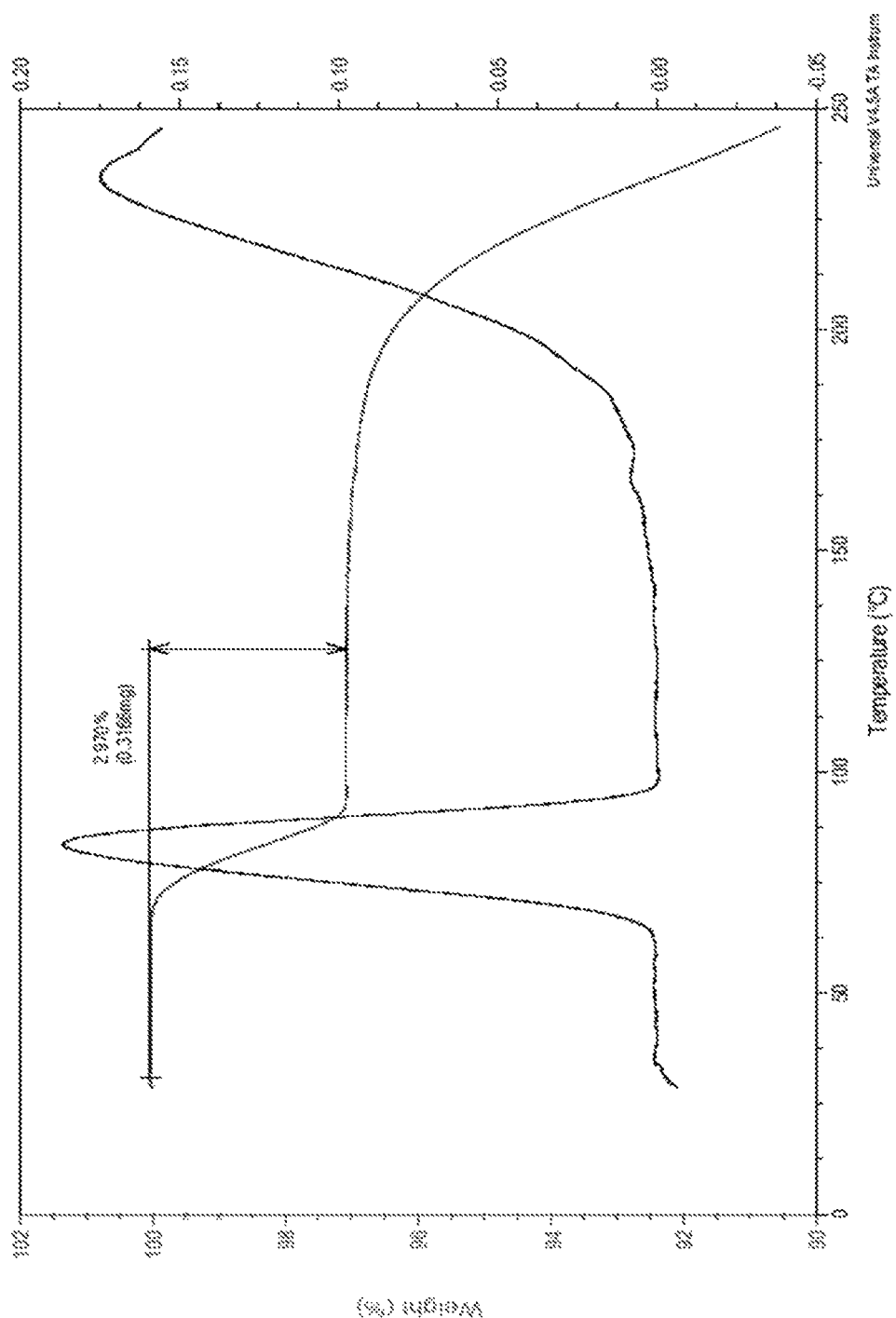
FIG. 24 is the characteristic TGA curve of empagliflozin DL-pipecolic acid co-crystals.

In another embodiment, the present invention provides empagliflozin DL-pipecolic acid co-crystals characterized by a thermogravimetric analysis (TGA) curve substantially in accordance with FIG. 24.

In another embodiment, the present invention provides empagliflozin DL-pipecolic acid co-crystals characterized by X-Ray powder diffraction (XRD) pattern substantially in accordance with FIG. 21, a $^1$H NMR Spectrum substantially in accordance with FIG. 22; a differential scanning calorimetry (DSC) thermogram substantially in accordance with FIG. 23 and a thermogravimetric analysis (TGA) curve substantially in accordance with FIG. 24.

The solid forms of SGLT2 inhibitors as described above may have greater stability, bioavailability, and having desired pharmacological, pharmacokinetic and pharmacodynamic effects as compared to the SGLT2 inhibitor individually.

In another embodiment, the present invention provides a pharmaceutical composition comprising at least one of the solid forms of SGLT2 inhibitors described above and at least one or more pharmaceutically acceptable excipients.

The present invention is further directed to methods for the treatment and or prevention of glucose related disorders. As used herein, the term "glucose related disorder" shall be defined as any disorder, which is characterized by or is developed as a consequence of elevated glucose levels. Glucose-related disorders shall include diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glucose, hyperlipidemia, obesity, hypertriglyceridemia, Syndrome X, diabetic complications, atherosclerosis, or hypertension. In particular, the "glucose related-disorder" is diabetes mellitus (type 1 and type 2 diabetes mellitus, etc.), diabetic complications (such as diabetic retinopathy, diabetic neuropathy, diabetic nephropathy), obesity, or postprandial hyperglycemia.

Solid forms of SGLT2 inhibitors were characterized by one or more of the techniques such as PXRD, TGA, DSC and IR techniques.

The X-Ray powder diffraction can be measured by X-ray powder diffractometer equipped with a Cu-anode ([λ]=1.54 Angstrom), X-ray source operated at 30 kV, 15 mA. Two-theta calibration is performed using an NIST SRM 640c Si standard. The sample was analyzed using the following instrument parameters: measuring range=3-45° 2θ; step width=0.020°; and scan speed=5° 2θ/minute; or by using PANalytical X'per³pro X-ray powder Diffractometer equipped with a Cu-anode ([λ]=1.54 Angstrom), X-ray source operated at 45 kV, 40 mA. Two-theta calibration is performed using an NIST SRM 640c Si standard. The sample was analyzed using the following instrument parameters: measuring range=3-45° 2θ; step size=0.01°; and Time per step=43 sec.

All TGA data reported herein were analyzed using TGA Q500 V 20.13 build 39 in platinum pan with a temperature rise of about 10° C./min in the range of about 30° C. to about 250° C.

All DSC data reported herein were analyzed in hermitically sealed aluminium pan, with a blank hermitically sealed aluminium pan as the reference and were obtained using DSC (DSC Q200, TA instrumentation, Waters) at a scan rate of 10° C. per minute with an Indium standard.

Or in hermitically sealed pinhole aluminium pan, with a blank hermitically sealed aluminium pan as the reference and were obtained using DSC (DSC Q200, TA instrumentation, Waters) at a scan rate of 10° C. per minute with an Indium standard.

As used herein, unless otherwise noted, the term "substantially pure form" shall mean that the percent of impurities in the isolated solid forms is less than about 5% by weight as measured by HPLC, preferably less than about 2%, more preferably less than about 1%, most preferably less than about 0.5%.

EXAMPLES

The present invention is further illustrated by the following examples, which are provided by way of illustration only and should not be construed to limit the scope of the invention.

Example 1: Preparation of Canagliflozin

In a round bottom flask equipped with reflux condenser, 1-(1-methoxyglucopyranosyl)-4-methyl-3-[5-(4-fluorophenyl)-2-thienylmethyl]-benzene (10 gms) was dissolved in mixture of methylene chloride (100 ml) and acetonitrile (20 ml) at 25-30° C. under nitrogen atmosphere. Triethyl silane (7.35 gms) was added and the reaction mass was stirred for 10 min at 25-30° C. The reaction mass was cooled to −45 to −40° C., added drop wise boron trifluoride ethyl ether complex (8 ml) and the mixture was stirred for 1.0 hr at same temperature. Further, the reaction mass was stirred at 0-5° C. for 2 hrs and quenched by adding saturated sodium bicarbonate solution (100 ml). The resulting organic layer was separated, washed with water (50 ml) and the organic solvent was distilled out under vacuum to obtain Canagliflozin (8.5 gms).

HPLC purity: 88.249%,
Alpha isomer content by HPLC: 2.76%.

Example 2: Preparation of Canagliflozin DL-Pipecolic Acid Co-Crystal: (Ethanol+Heptane)

To a round bottom flask equipped with reflux condenser, ethanol (100 ml) was added followed by Canagliflozin (5 gms; alpha isomer content by HPLC: 2.76%). The contents were heated to 55-60° C. and DL-Pipecolic acid (1.74 gms; source: Alfa aesar) was added at 55-60° C. The reaction mass was stirred for 20 min at 55-60° C., cooled to 25-30° C. and heptane (50 ml) was added. The reaction mass was stirred for 30 min at 55-60° C., cooled to 25-30° C. and stirred for 15 hrs at the same temperature. The solid obtained was filtered, washed with ethanol (10 ml) and suck dried for 30 min. To the resulting wet solid (HPLC purity: 99.48%, alpha isomer content: 0.126%) ethanol (75 ml) was added at 25-30° C., the reaction mass was raised to reflux and stirred for 10 min at reflux. The reaction mass was further cooled to 25-30° C. and stirred for 3 hrs at 25-30° C. The resulting solid was filtered, washed with ethanol (5 ml) and dried under vacuum at 75-80° C. for 5 hrs to obtain Canagliflozin DL-pipecolic acid co-crystal (2.5 gms).

HPLC purity: 99.88%, Alpha isomer content by HPLC: <0.05%, The PXRD is set forth in FIG. 01, The $^1$H NMR is set forth in FIG. 02, The DSC thermogram is set forth in FIG. 03, The TGA is set forth in FIG. 04, The IR is set forth in FIG. 05.

Example 3: Preparation of Canagliflozin DL-pipecolic Acid Co-Crystal: (ethanol+ethyl acetate)

To a round bottom flask equipped with reflux condenser, ethanol (10 ml) and ethyl acetate (50 ml) was added followed by canagliflozin (5 gm) and stirred for 10 min at 25-30° C. DL-Pipecolic acid (1.74 gm) was added; the contents were heated to reflux and stirred for 30 min. Then the reaction mass was cooled to 25-30° C. and the solid was filtered. The wet solid thus obtained was added into the mixture of ethanol (10 ml) and ethyl acetate (50 ml) and heated to reflux. The reaction mass was further allowed to cool to 25-30° C. and the solids were filtered to get Canagliflozin DL-pipecolic acid co-crystal (4 gms). HPLC purity: 99.5%.

Example 4: Preparation of Canagliflozin L-pipecolic Acid Co-Crystal: (ethanol+heptane)

To a round bottom flask equipped with reflux condenser, ethanol (100 ml), Canagliflozin (5 gms) and L-Pipecolic acid (1.74 gms) were added and reaction mass was allowed to raise to 70-75° C. Cooled the reaction mass to 55-60° C. and heptane (50 ml) was added. The reaction mass was further cooled to 25-30° C. and filtered the solid. The resulting wet solid was recrystallized from ethanol (75 ml) to obtain Canagliflozin L-pipecolic acid co-crystal (3.5 gm).

Example 5: Preparation of Canagliflozin L-pipecolic Acid Co-Crystal: (ethanol+ethyl acetate)

To a round bottom flask equipped with reflux condenser, Canagliflozin (5 gm), ethanol (10 ml) and ethyl acetate (50 ml) were added and the reaction mass was stirred for 10 min at 25-30° C. L-Pipecolic acid (1.74 gm) was added, the reaction mass was allowed to rise to reflux and stirred for 30 min. Then the reaction mass was cooled to 25-30° C. and the solid was filtered. To the resulting wet solid, ethanol (10 ml) and ethyl acetate (50 ml) was added and raised the temperature of the reaction mass to reflux. The reaction mass was further cooled to 25-30° C. and the solids were filtered to get Canagliflozin L-pipecolic acid co-crystal (3.5 gms).

Example 6: Preparation of Canagliflozin D-pipecolic Acid Co-Crystal: (ethanol+heptane)

To a round bottom flask equipped with reflux condenser, ethanol (100 ml), Canagliflozin (5 gms) and D-Pipecolic acid (1.74 gms) were added and the reaction mass was heated to 70-75° C. The contents of the flask were allowed to cool to 55-60° C. and added heptane (50 ml). Cooled the reaction mass further to 25-30° C. and the solid was filtered. The resulting wet solid was recrystallized from ethanol (75 ml) to obtain Canagliflozin D-pipecolic acid co-crystal (3.5 gm).

Example 7: Preparation of Canagliflozin D-pipecolic Acid Co-Crystal: (ethanol+ethyl acetate)

To a round bottom flask equipped with reflux condenser, Canagliflozin (5 gm), ethanol (10 ml) and ethyl acetate (50 ml) were added and stirred the contents for 10 min at 25-30° C. D-Pipecolic acid (1.74 gm) was added, heated the contents to reflux temperature and stirred for 30 min. Then, the reaction mass was cooled to 25-30° C. and the solid was filtered. The resulting wet solid was charged into the mixture of ethanol (10 ml) and ethyl acetate (50 ml), heated to reflux, cooled to 25-30° C. and the solids were filtered to get Canagliflozin D-pipecolic acid co-crystal (3.5 gms).

Example 8: Preparation of Canagliflozin Nicotinic Acid Co-Crystal

To a round bottom flask equipped with reflux condenser, Canagliflozin (2 gms), ethanol (40 ml), and nicotinic acid (0.6 gm) was added at 25-30° C. Heated the contents of the flask to 70-75° C. and allowed to cool to 25-30° C. The reaction mass was stirred for 5 hrs at 25-30° C. and filtered the solid to obtain Canagliflozin Nicotinic acid co-crystal (0.3 gm).

Example 9: Preparation of Canagliflozin pyrazine-2-carboxylic Acid Co-Crystal To a round bottom flask equipped with reflux condenser, Canagliflozin (2 gms) was dissolved in ethanol (40 ml), and added pyrazine-2-carboxylic acid (0.6 gm) at 25-30° C. Heat the contents to 70-75° C. and allowed to cool to 25-30° C. The reaction mass was stirred for 5 hrs at 25-30° C. and filtered the solid to obtain Canagliflozin pyrazine-2-carboxylic acid co-crystal (0.4 gm).

Example 10: Preparation of Canagliflozin Pyrazole Co-Crystal

To a round bottom flask equipped with reflux condenser, ethanol (100 ml), Canagliflozin (5 gms) and pyrazole (0.8 gms) were added and the reaction mass was heated to 70-75° C. The contents of the flask were allowed to cool to 55-60° C. and added heptane (50 ml). Cooled the reaction mass further to 25-30° C. and the solid was filtered. The resulting wet solid was purified from mixture of ethanol (75 ml) and n-heptane (75 ml) to obtain Canagliflozin pyrazole co-crystal co-crystal (4 gm).

Example 11: Preparation of Canagliflozin

To a round bottom flask equipped with reflux condenser, ethyl acetate (30 ml) and Canagliflozin DL-pipecolic acid co-crystal (5 gms) was added at 25-30° C. Sodium bicarbonate solution (2.5 gm dissolved in 50 ml water) was added to the reaction mass at 25-30° C. and stirred for 30 min at the same temperature. The resulting organic layer was washed with water and solvent from the organic layer was distilled completely under vacuum at below 45° C. Cyclohexane (30 ml) was added to the resulting residue at 25-30° C., stirred for 30 min at 25-30° C., filtered the solid and washed with cyclohexane (5 ml). The obtained solids are dried under vacuum at below 45° C. for 10.0 hrs to obtain amorphous canagliflozin (3.0 gms). HPLC purity: 99.8%.

Figure 6:
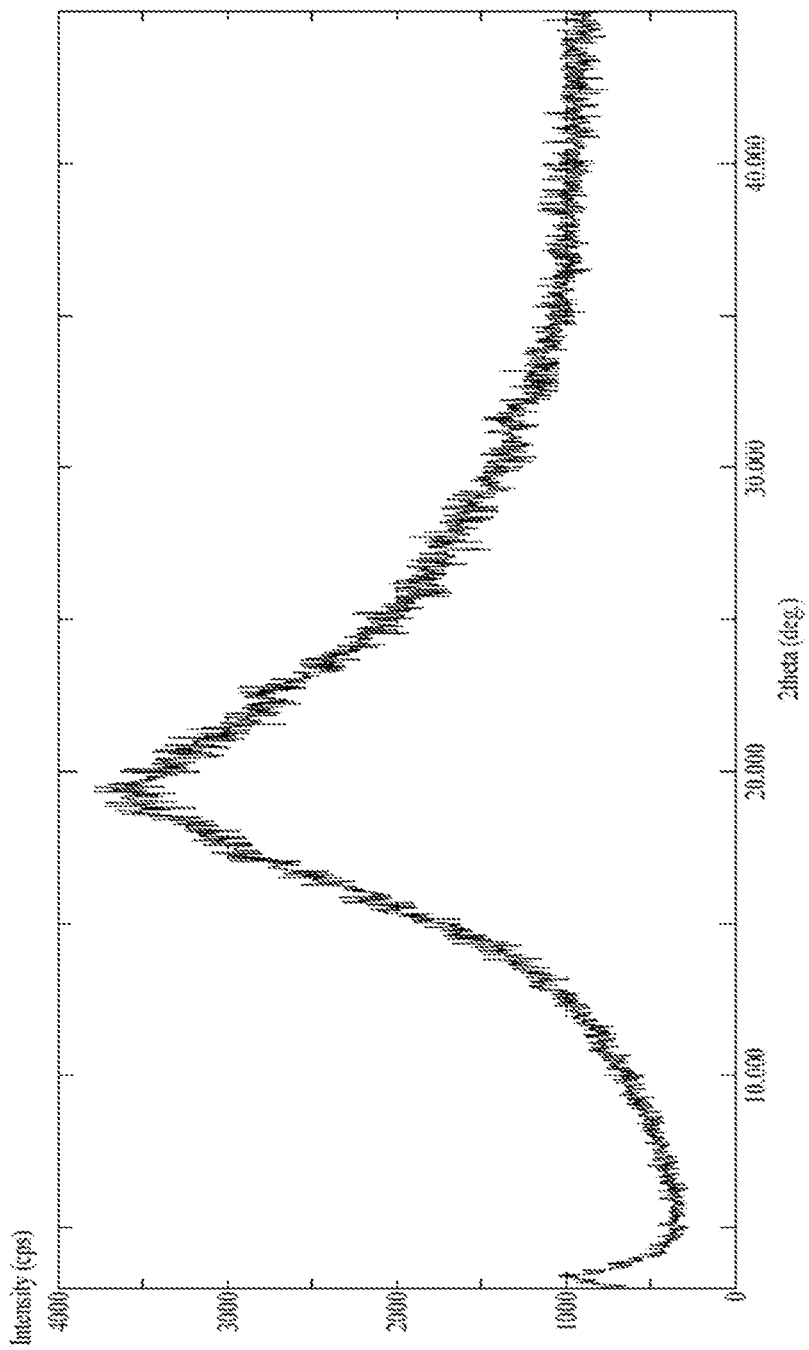
FIG. 6 is the characteristic powder XRD pattern of Canagliflozin obtained according to example 10 of the present invention.
Figure 7:
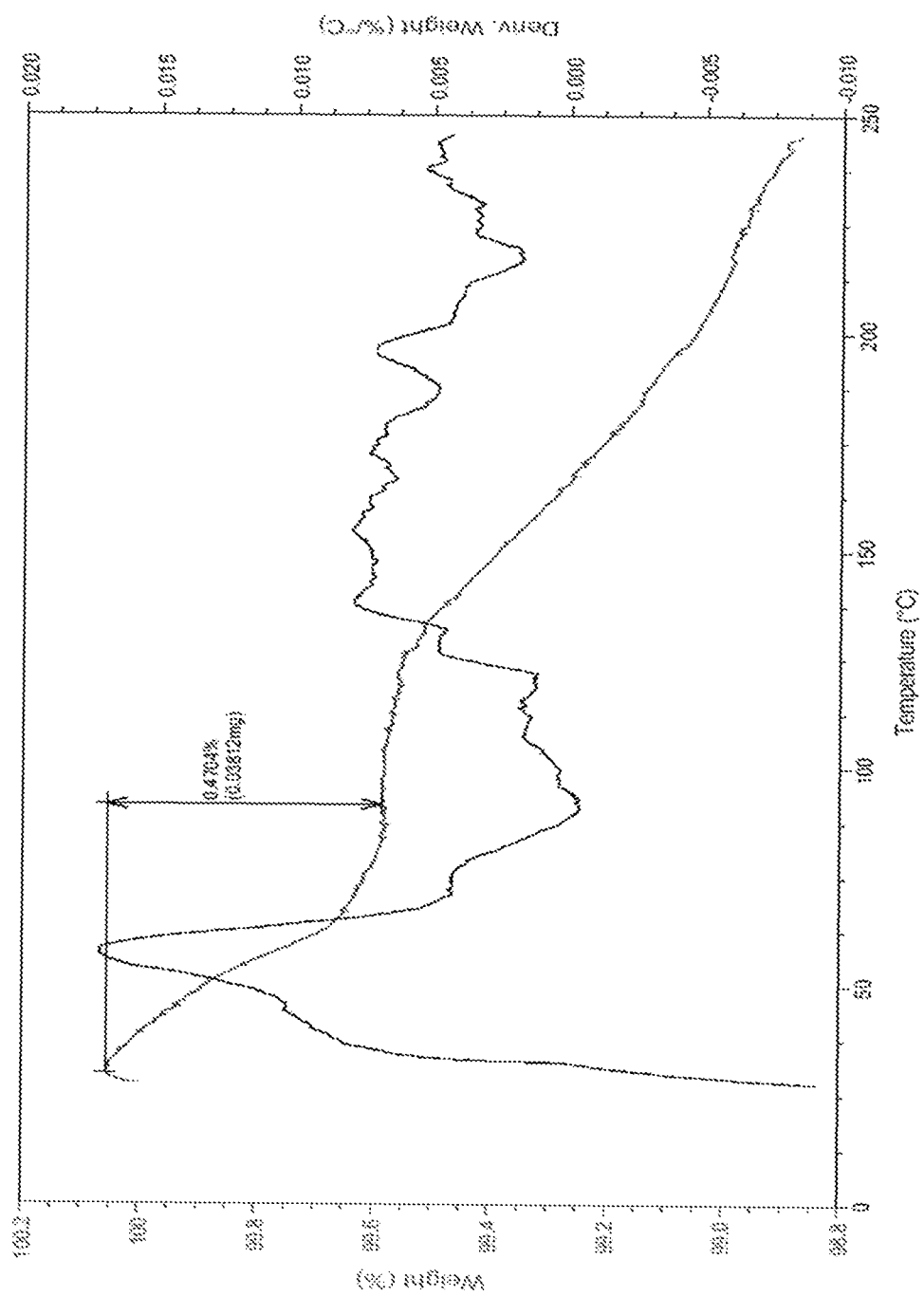
FIG. 7 is the characteristic TGA curve of Canagliflozin obtained according to example 10 of the present invention.
Figure 8:
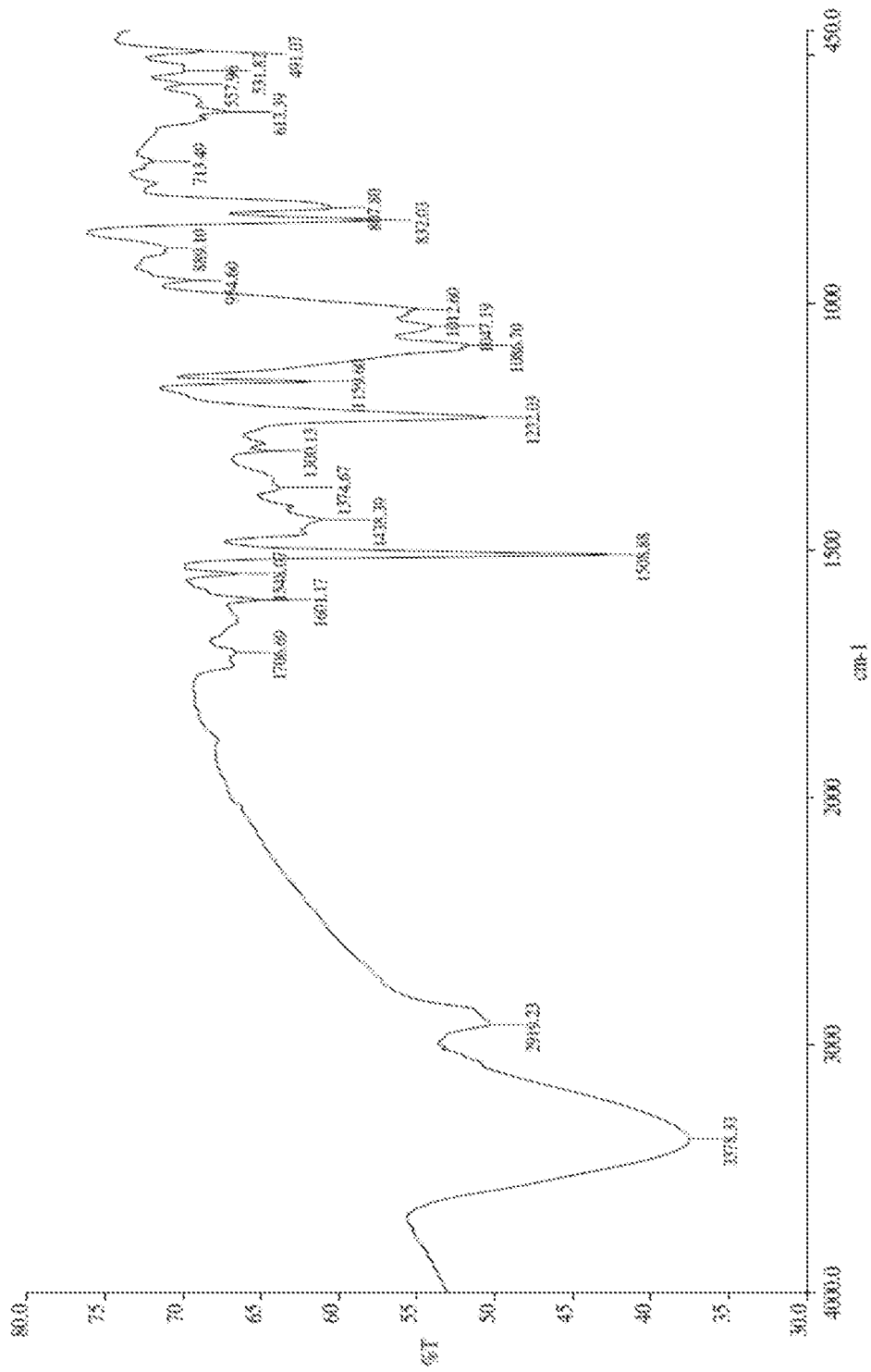
FIG. 8 is the characteristic IR spectrum of Canagliflozin obtained according to example 10 of the present invention.

Alpha isomer content by HPLC: <0.05%, The PXRD is set forth in FIG. 06, The TGA is set forth in FIG. 07, The IR is set forth in FIG. 08.

Example 12: Preparation of Canagliflozin

To a round bottom flask equipped with reflux condenser, ethyl acetate (50 ml), Canagliflozin (5 g), methanol (2.5 ml) and diethyl ether (5 ml) were added and allowed to cool to 0-5° C. Ammonia gas was purged for 20 min at 0-5° C., filtered the resulting solids and washed with diethyl ether (10 ml). The obtained solid was dissolved in ethyl acetate (40 ml) at 25-30° C. and washed with water. The resulting organic layer was distilled out completely under vacuum at below 50° C. Cyclohexane (25 ml) was added to the resultant compound and stirred for 30 min at 25-30° C. The obtained solid was filtered, washed with cyclohexane (5 ml) and dried under vacuum at below 45° C. for 10 hrs to obtain amorphous canagliflozin (1 gm).

HPLC purity: 99.0%.

Example 13: Preparation of Dapagliflozin DL-pipecolic Acid Co-Crystals

To a round bottom flask equipped with reflux condenser, dapagliflozin (5 gms), isopropyl acetate (100 ml) and DL-pipecolic acid (1.5 gms) were added at room temperature and stirred the contents for 4 hrs at room temperature. The solid obtained was filtered, washed with isopropyl acetate (10 ml) and suck dried for 20 min. The resulting solid was dried under vacuum for 16 hrs at room temperature and further dried under vacuum for 7 hrs at 40° C. to obtain dapagliflozin DL-pipecolic acid co-crystals (4.7 gms).

The PXRD is set forth in FIG. 09, The $^1$H NMR is set forth in FIG. 10, The DSC thermogram is set forth in FIG. 11, The TGA is set forth in FIG. 12.

Example 14: Preparation of Dapagliflozin DL-pipecolic Acid Co-Crystals

To a round bottom flask equipped with reflux condenser, isopropyl acetate (20 ml) and DL-pipecolic acid (631 mg) were added at 20-25 C° and the reaction mixture was stirred for 10 mins. Dapagliflozin (2.0 gm) was added to the reaction mixture at 25-30° C. and stirred the contents for 24 hrs at 20-25° C. The solid obtained was filtered and washed with isopropyl acetate (5 ml). The obtained solid was dried under vacuum at 40-45° C. for 20 hrs to obtain dapagliflozin DL-pipecolic acid co-crystals (2.3 gms).

Example 15: Preparation of Dapagliflozin D-pipecolic Acid Co-Crystals

To a round bottom flask equipped with reflux condenser, isopropyl acetate (10 ml) and D-pipecolic acid (315 mg) were added at 20-25 C° and the reaction mixture was stirred for 10 mins. Dapagliflozin (1.0 gm) was added to the reaction mixture at 25-30° C. and stirred the contents for 24 hrs at 20-25° C. The solid obtained was filtered and washed with isopropyl acetate (3 ml). The obtained solid was dried under vacuum at 40-45° C. for 20 hrs to obtain dapagliflozin D-pipecolic acid co-crystals (1.2 gms).

The PXRD is set forth in FIG. 13.

Example 16: Preparation of Dapagliflozin L-pipecolic Acid Co-Crystals

To a round bottom flask equipped with reflux condenser, isopropyl acetate (10 ml) and L-pipecolic acid (315 mg) were added at 20-25 C° and the reaction mixture was stirred for 10 mins. Dapagliflozin (1.0 gm) was added to the reaction mixture at 25-30° C. and stirred the contents for 24 hrs at 20-25° C. The solid obtained was filtered and washed with isopropyl acetate (3 ml). The obtained solid was dried under vacuum at 40-45° C. for 20 hrs to obtain dapagliflozin L-pipecolic acid co-crystals (1.1 gms).

The PXRD is set forth in FIG. 14.

Example 17: Preparation of Dapagliflozin 2,3-butanediol Solvate (MTBE-heptane)

To a round bottom flask equipped with reflux condenser, dapagliflozin (0.5 gms) and MTBE (3 ml) were added at 20-25° C. and stirred the reaction mixture at 20-25° C. for 10 mins. 2,3-butanediol (110 mgs) was added and stirred the reaction mixture for 1 hr at 20-25° C. followed by heptane (1 mL) was added. Stirred the reaction mixture for 30 mins at 20-25° C., seed crystals of dapagliflozin 2,3-butanediol solvate (~20 mg) was added and stirred for 15 mins at 20-25° C. Heptane (9 mL) was added and stirred for 2 hrs at 20-25° C. The resulting solids was filtered under vacuum at 20-25° C., washed with heptane (3 mL), suck dried for 10 mins and finally dried at room temperature under vacuum for 24 hrs to obtain dapagliflozin 2,3-butanediol solvate (570 mg).

The PXRD is set forth in FIG. 15, The $^1$H NMR is set forth in FIG. 16, The DSC thermogram is set forth in FIG. 17, The TGA is set forth in FIG. 18.

Example 18: Preparation of Dapagliflozin 2,3-butanediol Solvate (isopropyl acetate-heptane)

To a round bottom flask equipped with reflux condenser, dapagliflozin (0.5 gms) and isopropyl acetate (2 ml) were added at 20-25° C. and stirred the reaction mixture at 20-25° C. for 10 mins. 2,3-butanediol (110 mgs) was added and stirred the reaction mixture for 1 hr at 20-25° C. followed heptane (1 ml) was added. Stirred the reaction mixture for 30 mins at 20-25° C., seed crystals of dapagliflozin 2,3-butanediol solvate (~20 mg) was added and stirred for 15 mins at 20-25° C. Heptane (9 ml) was added and stirred for 2 hrs at 20-25° C. The resulting solid was filtered under vacuum at 20-25° C., washed with heptane (3 mL), suck dried for 10 mins and finally dried at room temperature under vacuum for 24 hrs to obtain dapagliflozin 2,3-butanediol solvate (620 mg).

Example 19: Preparation of Amorphous Dapagliflozin (Methanol-water)

To a round bottom flask equipped with reflux condenser, dapagliflozin (5 gms) and methanol (15 ml) were added. The reaction mixture was heated to 60° C., stirred for 10 mins at 60° C. to obtain clear solution and then allowed to cool to 5° C. To the resulting solution, first portion of water (13.5 ml) was added, seeded with amorphous dapagliflozin (~30 mg) and stirred for 30 mins at 0-5° C. To the resulting reaction mixture remaining water was added in multiple lots (3 lots, 40 ml for each lot) with stirring for 30 mins at 0-5° C. after each addition and finally stirring for 2 hrs at 0-5° C. The resulting solid was filtered and washed with water (100 ml). The resulting solid was suck dried for 2 hrs under vacuum and further dried at 35° C. for 24 hrs to obtain amorphous dapagliflozin (4.5 gms).

Figure 19:
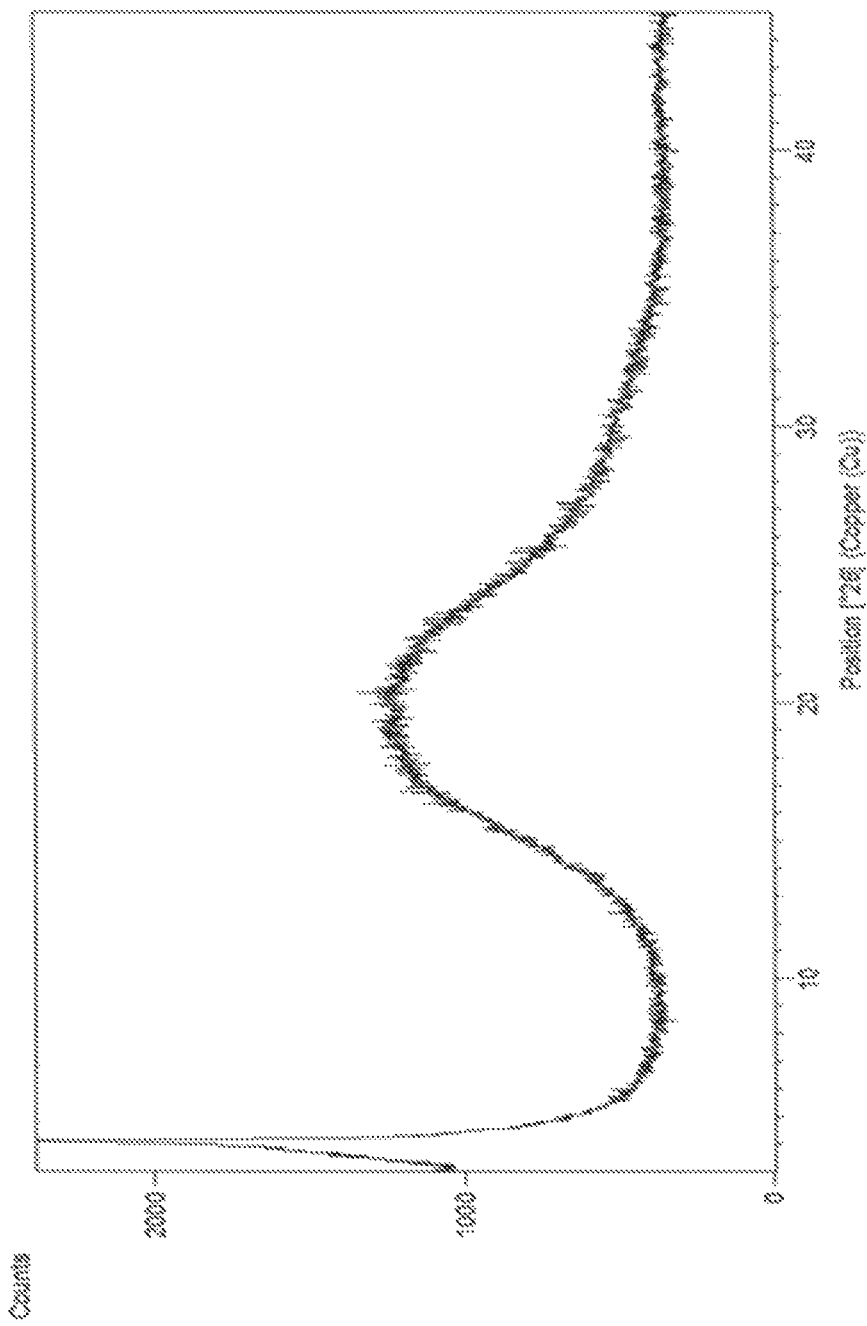
FIG. 19 is the characteristic powder XRD pattern of amorphous dapagliflozin.
Figure 20:
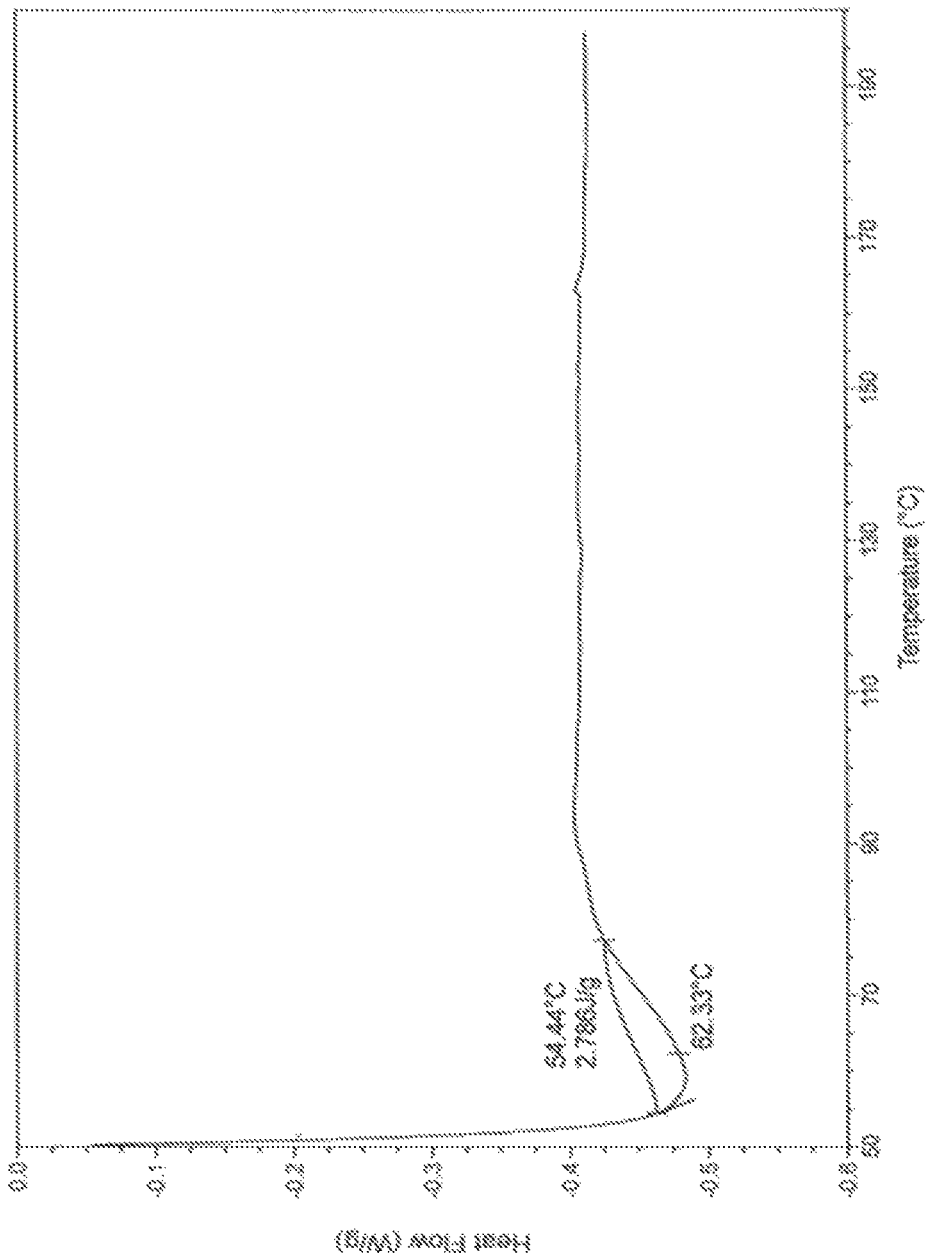
FIG. 20 is the characteristic DSC thermogram of amorphous dapagliflozin.

The PXRD is set forth in FIG. 19, The DSC thermogram is set forth in FIG. 20.

Example 20: Preparation of Amorphous Dapagliflozin (methanol-water)

To a round bottom flask equipped with reflux condenser, dapagliflozin DL-pipecolic acid co-crystals (1 gm) and water (10 ml) were added at room temperature and the reaction mixture was stirred for 5 mins. 1N sodium hydroxide (1 ml) was added and the reaction mixture was stirred for 5 mins at room temperature. Methanol (5 ml) was added and the reaction mixture was heated to 60° C., stirred for 10 mins at 60° C. to obtain clear solution and allowed to cool to 5° C. To the resulting solution, first portion of water (4 ml) was added, seeded with amorphous dapagliflozin (~10 mg) and stirred for 30 mins at 0-5° C. To the resulting reaction mixture, remaining water was added in multiple lots (3 lots, 10 ml for each lot) with stirring for 30 mins at 0-5° C. after each addition and finally stirring for 2 hrs at 0-5° C. The resulting solid was filtered and washed with water (10 ml). The resulting solid was suck dried for 2 hrs under vacuum and further dried at 35° C. for 24 hrs to obtain amorphous dapagliflozin (0.85 gms).

Example 21: Preparation of Amorphous Dapagliflozin (MTBE-Heptane)

To a round bottom flask equipped with reflux condenser, dapagliflozin (2 gms) and MTBE (16 ml) were added. The reaction mass was heated to 55° C. and stirred for 15 mins at 55° C. The resulting solution was added drop wise to pre-cooled heptane (96 ml) at 15° C. The reaction mixture was stirred for 30 mins at 15° C., filtered the solids and washed with heptane (10 ml). The resulting solid was dried at 35° C. under vacuum for 16 hrs and at 55° C. under vacuum for 12 hrs to obtain amorphous dapagliflozin (1.9 gms).

Example 22: Preparation of Amorphous Dapagliflozin (MTBE-Cyclohexane)

To a round bottom flask equipped with reflux condenser, dapagliflozin (2 gms) and MTBE (16 ml) were added. The reaction mixture was heated to 55° C. and stirred for 15 mins at 55° C. The resulting reaction mixture was added drop wise to pre-cooled cyclohexane (96 ml) at 15° C. The reaction mixture was stirred at 15° C. for 30 mins, filtered and washed with cyclohexane (10 ml). The resulting solid was dried at 35° C. under vacuum for 16 hrs and further dried at 55° C. under vacuum for 12 hrs to get amorphous dapagliflozin (1.85 gms).

Example 23: Preparation of Amorphous Dapagliflozin (MTBE-Heptane)

To a round bottom flask equipped with reflux condenser, dapagliflozin DL-pipecolic acid co-crystals (2 gms) and ethyl acetate (30 mL) were added and stirred the reaction mixture for 5 mins at room temperature. Water (30 mL) was added and stirred the mixture for 5 mins at room temperature. 1N Sodium hydroxide solution (3.7 ml) was added to the reaction mixture and the mixture was stirred at room temperature for 10 mins. The organic layer was separated and the aqueous layer was extracted with ethyl acetate (20 ml). The combined organic layer was washed with water (20 ml) and evaporated completely at 50° C. The obtained residue was co-distilled with heptane (20 ml) under vacuum at 50° C. The resulting residue was dissolved in MTBE (6.5 mL) at room temperature and heptane (26 mL) was added at 15° C. The reaction mixture was stirred at 15° C. for 30 mins, filtered the solids and dried at 35° C. for 16 hrs and further dried at 55° C. under vacuum for 12 hrs to obtain amorphous dapagliflozin (980 mg).

Example 24: Preparation of Amorphous Dapagliflozin (methyl acetate)

To a round bottom flask equipped with reflux condenser, dapagliflozin DL-pipecolic acid co-crystals (1 gm) and water (10 ml) were charged at room temperature and stirred the reaction mixture for 5 mins. 1N sodium hydroxide (1 ml) was added and stirred the reaction mixture for 5 mins at room temperature. Methyl acetate (10 ml) was added to the reaction mixture, stirred the solution for 10 mins at room temperature and the obtained layers were separated. The aqueous layer was extracted with methyl acetate (10 ml) and the combined organic layers were washed with water (10 ml). The organic layer was distilled at 50° C. under vacuum to obtain amorphous dapagliflozin (0.4 gms).

Example 25: Preparation of Amorphous Dapagliflozin (Methyl tertiary butyl ether)

To a round bottom flask equipped with reflux condenser, dapagliflozin DL-pipecolic acid co-crystals (1 gm) and water (10 ml) were added at room temperature and the reaction mixture was stirred for 5 mins. 1N sodium hydroxide (1 ml) was added and the reaction mixture was stirred for 5 mins at room temperature. Methyl tertiary butyl ether (10 mL) was added to the reaction mixture, stirred the solution for 10 mins at room temperature and the obtained layers were separated. The aqueous layer was extracted with methyl tertiary butyl ether (10 ml) and the combined organic layers were washed with water (10 mL). The organic layer was distilled at 50° C. under vacuum to obtain amorphous dapagliflozin (0.8 gms).

Example 26: Preparation of Amorphous Dapagliflozin (Isopropyl Acetate)

To a round bottom flask equipped with reflux condenser, dapagliflozin DL-pipecolic acid co-crystals (1 gm) and water (10 ml) were charged at room temperature and stirred the reaction mixture for 5 mins. 1N sodium hydroxide (1 ml) was added and the reaction mixture was stirred for 5 mins at room temperature. Isopropyl acetate (10 ml) was added to the reaction mixture, stirred the solution for 10 mins at room temperature and the obtained layers were separated. The aqueous layer was extracted with Isopropyl acetate (10 ml) and the combined organic layers were washed with water (10 ml). The organic layer was distilled at 50° C. under vacuum to obtain amorphous dapagliflozin (0.8 gms).

Example 27: Preparation of Amorphous Dapagliflozin (Methanol-water)

To a round bottom flask equipped with reflux condenser, dapagliflozin (4 gms) and methanol (12 ml) were added. The reaction mixture was heated to 60° C., stirred for 10 mins at 60° C. to obtain clear solution and cooled to room temperature. To the resulting solution, water (100 ml) was added at room temperature. The reaction mixture was stirred at room temperature for 10 mins, cooled to 0-5° C. and stirred for 6 hrs. The resulting solid was filtered and washed with chilled water (20 ml). The resulting solid was dried at room temperature under vacuum for 5 hrs and further dried at 40° C. under vacuum for 6 hrs to obtain amorphous dapagliflozin (3.0 gms).

Example 28: Preparation of Amorphous Dapagliflozin (Methanol-water)

To a round bottom flask equipped with reflux condenser, dapagliflozin (4 gms) and methanol (12 ml) were added. The reaction mixture was heated to 60° C., stirred for 10 mins at 60° C. and cooled to room temperature. The resulting solution was added drop wise to pre-cooled water (125 ml) at 0-5° C. The mixture was stirred at 0-5° C. for 6 hrs, filtered the solid and washed with chilled water (25 ml). The resulting solid was dried at 30-35° C. under vacuum for 16 hrs and further at 50-55° C. under vacuum for 12 hrs to obtain amorphous dapagliflozin (3.0 gms).

Example 29: Preparation of Empagliflozin DL-pipecolic Acid Co-Crystals

To a round bottom flask equipped with reflux condenser, Empagliflozin (10 gm), DL-pipecolic acid (5.75 gm) and n-butanol (100 ml) were added and raised the temperature to 80° C. DM water (5 ml) was added and stirred the reaction mass for 30 min. The resulted clear solution was allowed to cool to 25° C. and stirred for 30 min. The suspension was further allowed to cool to 3° C., filtered the product and washed with n-butanol (20 ml). The obtained solid was dried under vacuum for 8 hrs at 40° C. to obtain empagliflozin DL-pipecolic acid co-crystals (12.8 gms).

The PXRD is set forth in FIG. 21, The $^1$H NMR is set forth in FIG. 22, The DSC thermogram is set forth in FIG. 23, The TGA is set forth in FIG. 24.

Example 30: Preparation of Empagliflozin DL-pipecolic Acid Co-Crystals

To a round bottom flask equipped with reflux condenser, Empagliflozin (1 gm), pipecolic acid (0.572 gm) and n-butanol (10 ml) were added and raised the temperature to 80° C. DM water (0.5 ml) was added and stirred the reaction mass for 30 min. The resulted clear solution was cooled to 25° C. and stirred the suspension for 30 min. The suspension was further cooled to 3° C., washed with n-butanol (2 ml) and suck dried for 30 min. The obtained solid was dried under vacuum for 8 hrs at 45° C. to obtain empagliflozin DL-pipecolic acid co-crystals (1.1 gms).

It will be understood that various modifications may be made to the embodiments disclosed herein. Therefore, the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

The invention claimed is:

1. A process for the preparation of empagliflozin DL-pipecolic acid co-crystals, comprising:
    a) providing a solution or suspension comprising empagliflozin and DL-pipecolic acid in one or more solvents; and
    b) isolating the empagliflozin DL-pipecolic acid co-crystals.

2. The process of claim 1, wherein the solvents are selected from the group consisting of an ester, an alcohol, an ether, a ketone, an aliphatic hydrocarbon, a halogenated hydrocarbon, a nitrile, water, and mixtures thereof.

3. The process of claim 2, wherein the solvent is one or more of n-butanol, ethanol and acetone.

* * * * *